(12) United States Patent
Mayer et al.

(10) Patent No.: US 9,757,237 B2
(45) Date of Patent: Sep. 12, 2017

(54) METHOD FOR FUSING A HUMAN OR ANIMAL JOINT AS WELL AS FUSION DEVICE AND TOOL SET FOR CARRYING OUT THE METHOD

(71) Applicant: WW Technology AG, Schlieren (CH)

(72) Inventors: Jörg Mayer, Niederlenz (CH); Mario Lehmann, Les Pommerats (CH); Stephanie Mehl, Zug (CH); Elmar Mock, Colombier (CH); Andrea Mueller, Winterthur (CH); Milica Berra, Schlieren (CH); Urs Weber, Evilard (CH)

(73) Assignee: WW TECHNOLOGY AG, Schlieren (CH)

( * ) Notice: Subject to any disclaimer, the term of this patent is extended or adjusted under 35 U.S.C. 154(b) by 0 days.

(21) Appl. No.: 14/593,332

(22) Filed: Jan. 9, 2015

(65) Prior Publication Data
US 2015/0119993 A1 Apr. 30, 2015

Related U.S. Application Data

(62) Division of application No. 13/124,857, filed as application No. PCT/CH2009/000337 on Oct. 20, 2009, now Pat. No. 8,951,254.

(Continued)

(51) Int. Cl.
*A61F 2/30* (2006.01)
*A61B 17/16* (2006.01)
(Continued)

(52) U.S. Cl.
CPC ............ *A61F 2/30* (2013.01); *A61B 17/1617* (2013.01); *A61B 17/1682* (2013.01);
(Continued)

(58) Field of Classification Search
CPC .................................................. A61B 17/0642
See application file for complete search history.

(56) References Cited

U.S. PATENT DOCUMENTS 2,817,339 A * 12/1957 Sullivan ............ A61B 17/0644
606/221
3,454,011 A * 7/1969 Wagner ............ A61B 17/06166
606/224

(Continued)

FOREIGN PATENT DOCUMENTS

CN 1494398 5/2004
CN 1688263 10/2005
(Continued)

OTHER PUBLICATIONS

Nozaki et al., Comparison of elastic versus rigid suture material for peripheral sutures in tendon repair, 2012, Elsevier, Clinical Biomechanics 27, pp. 506-510.*

(Continued)

*Primary Examiner* — Zade Coley
(74) *Attorney, Agent, or Firm* — Rankin, Hill & Clark LLP

(57) ABSTRACT

The fusion device for fusing a synovial joint of a human or animal patient, in particular a human facet joint, finger joint or toe joint, includes two pin-shaped anchorage portions and arranged therebetween a stabilization portion. The anchorage portions include a thermoplastic material which is liquefiable by mechanical vibration. The stabilization portion preferably has a surface which is equipped for enhancing osseointegration. The anchorage portions have a greater thickness and a greater depth than the stabilization portion. Then the fusion device is pushed between the articular surfaces and mechanical vibration, in particular ultrasonic vibration, is applied to the proximal face of the fusion device. Thereby the liquefiable material is liquefied where in (Continued)

contact with the bone tissue and penetrates into the bone tissue, where after re-solidification it constitutes a positive fit connection between the fusion device and the bone tissue.

27 Claims, 10 Drawing Sheets

Related U.S. Application Data

(60) Provisional application No. 61/107,011, filed on Oct. 21, 2008, provisional application No. 61/107,757, filed on Oct. 23, 2008, provisional application No. 61/149,809, filed on Feb. 4, 2009, provisional application No. 61/187,466, filed on Jun. 16, 2009.

(51) Int. Cl.
*A61B 17/68* (2006.01)
*A61F 2/42* (2006.01)
*A61F 2/46* (2006.01)
*A61B 17/064* (2006.01)
*A61B 17/00* (2006.01)
*A61F 2/00* (2006.01)
*A61F 2/44* (2006.01)
*A61F 2/28* (2006.01)
*A61B 17/17* (2006.01)

(52) U.S. Cl.
CPC .......... *A61B 17/1686* (2013.01); *A61B 17/68* (2013.01); *A61F 2/30767* (2013.01); *A61F 2/42* (2013.01); *A61F 2/4611* (2013.01); *A61B 17/0642* (2013.01); *A61B 17/1775* (2016.11); *A61B 17/1782* (2016.11); *A61B 2017/00831* (2013.01); *A61F 2/0077* (2013.01); *A61F 2/30965* (2013.01); *A61F 2/4405* (2013.01); *A61F 2/4455* (2013.01); *A61F 2002/2817* (2013.01); *A61F 2002/2835* (2013.01); *A61F 2002/3008* (2013.01); *A61F 2002/30062* (2013.01); *A61F 2002/30065* (2013.01); *A61F 2002/3093* (2013.01); *A61F 2002/30121* (2013.01); *A61F 2002/30123* (2013.01); *A61F 2002/30166* (2013.01); *A61F 2002/30622* (2013.01); *A61F 2002/30841* (2013.01); *A61F 2002/4631* (2013.01); *A61F 2210/0004* (2013.01); *A61F 2210/0071* (2013.01); *A61F 2230/0028* (2013.01); *A61F 2250/0098* (2013.01); *A61F 2310/00023* (2013.01); *A61F 2310/00131* (2013.01); *A61F 2310/00239* (2013.01); *A61F 2310/00796* (2013.01)

(56) References Cited

U.S. PATENT DOCUMENTS

| | | | |
|---|---|---|---|
| 3,716,058 A * | 2/1973 | Tanner, Jr. | A61B 17/064 606/221 |
| D268,870 S | 5/1983 | Dohogne | |
| D282,207 S | 1/1986 | Kalen | |
| D286,180 S | 10/1986 | Korthoff | |
| D298,168 S | 10/1988 | Herbst et al. | |
| 4,994,063 A * | 2/1991 | Garner | A61B 17/0642 606/75 |
| D357,534 S | 4/1995 | Hayes | |
| D359,557 S | 6/1995 | Hayes | |
| D374,283 S | 10/1996 | Michelson | |
| D382,056 S | 8/1997 | Kammerer | |
| 5,755,721 A | 5/1998 | Hearn | |
| D397,436 S | 8/1998 | Michelson | |
| D420,132 S | 2/2000 | Bucholz et al. | |
| D433,506 S | 11/2000 | Asfora | |
| 6,179,840 B1 * | 1/2001 | Bowman | A61B 17/0401 128/899 |
| 6,554,852 B1 * | 4/2003 | Oberlander | A61B 17/0401 606/104 |
| 6,921,264 B2 | 7/2005 | Mayer et al. | |
| 7,008,226 B2 | 3/2006 | Mayer et al. | |
| 7,104,999 B2 * | 9/2006 | Overaker | A61B 17/0642 606/104 |
| 7,223,269 B2 | 5/2007 | Chappuis | |
| 7,335,205 B2 | 2/2008 | Aeschlimann et al. | |
| 7,344,539 B2 * | 3/2008 | Serhan | A61B 17/0642 606/247 |
| 7,357,804 B2 | 4/2008 | Binder, Jr. et al. | |
| D574,495 S | 8/2008 | Petersen | |
| D574,957 S | 8/2008 | Petersen | |
| 2002/0032483 A1 * | 3/2002 | Nicholson | A61B 17/1757 623/17.11 |
| 2002/0077702 A1 | 6/2002 | Castro | |
| 2002/0198533 A1 | 12/2002 | Geisler et al. | |
| 2003/0167072 A1 * | 9/2003 | Oberlander | A61B 17/0401 606/232 |
| 2003/0232198 A1 * | 12/2003 | Lamberti | A61L 27/26 428/423.1 |
| 2004/0030341 A1 * | 2/2004 | Aeschlimann | A61B 17/00491 606/232 |
| 2004/0038180 A1 | 2/2004 | Mayer et al. | |
| 2004/0267278 A1 * | 12/2004 | Overaker | A61B 17/0642 606/104 |
| 2005/0124993 A1 | 6/2005 | Chappuis | |
| 2005/0159813 A1 | 7/2005 | Molz, IV | |
| 2006/0074434 A1 | 4/2006 | Wenstrom, Jr. et al. | |
| 2006/0085068 A1 | 4/2006 | Barry | |
| 2006/0105295 A1 | 5/2006 | Mayer et al. | |
| 2006/0111779 A1 | 5/2006 | Petersen | |
| 2006/0111782 A1 | 5/2006 | Petersen | |
| 2006/0190081 A1 | 8/2006 | Kraus et al. | |
| 2006/0241601 A1 | 10/2006 | Trautwein et al. | |
| 2007/0093834 A1 * | 4/2007 | Stevens | A61B 17/0401 606/279 |
| 2007/0093839 A1 * | 4/2007 | Beckendorf | A61B 17/0642 606/75 |
| 2007/0162030 A1 * | 7/2007 | Aranyi | A61B 17/064 606/75 |
| 2007/0198091 A1 | 8/2007 | Boyer et al. | |
| 2007/0233150 A1 | 10/2007 | Blain et al. | |
| 2007/0250065 A1 | 10/2007 | Efron et al. | |
| 2007/0265622 A1 | 11/2007 | Aeschlimann et al. | |
| 2007/0265704 A1 | 11/2007 | Mayer et al. | |
| 2007/0270833 A1 | 11/2007 | Bonutti et al. | |
| 2007/0276388 A1 * | 11/2007 | Robertson | A61B 17/0057 606/75 |
| 2008/0021474 A1 | 1/2008 | Bonutti et al. | |
| 2008/0039845 A1 | 2/2008 | Bonutti et al. | |
| 2008/0065093 A1 | 3/2008 | Assell et al. | |
| 2008/0109080 A1 | 5/2008 | Aeschlimann et al. | |
| 2008/0154374 A1 | 6/2008 | Labrom | |
| 2008/0255622 A1 | 10/2008 | Mickiewicz et al. | |
| 2008/0255666 A1 | 10/2008 | Fisher et al. | |
| 2008/0255667 A1 | 10/2008 | Horton | |
| 2009/0018560 A1 | 1/2009 | Mayer et al. | |
| 2009/0036927 A1 | 2/2009 | Vestgaarden | |
| 2009/0053011 A1 * | 2/2009 | Brackett | F16B 15/0015 411/457 |
| 2009/0076551 A1 | 3/2009 | Petersen | |
| 2009/0125066 A1 | 5/2009 | Kraus et al. | |
| 2009/0131947 A1 | 5/2009 | Aeschlimann et al. | |
| 2009/0131986 A1 | 5/2009 | Lee et al. | |
| 2009/0171394 A1 | 7/2009 | Abdou | |
| 2009/0177205 A1 | 7/2009 | McCormack et al. | |
| 2009/0204152 A1 | 8/2009 | Blain | |
| 2009/0234397 A1 | 9/2009 | Petersen | |
| 2009/0264928 A1 | 10/2009 | Blain | |
| 2011/0118744 A1 | 5/2011 | Lehmann et al. | |

(56) References Cited

U.S. PATENT DOCUMENTS

2012/0109197 A1    5/2012  Carl et al.
2013/0190879 A1    7/2013  Assell et al.

FOREIGN PATENT DOCUMENTS

| | | | |
|---|---|---|---|
| CN | 1921809 | 2/2007 | |
| CN | 101217917 | 7/2008 | |
| DE | 10135771 | 2/2003 | |
| EP | 2596764 | 5/2013 | |
| JP | 07-008514 | 1/1995 | |
| JP | 2001525224 | 12/2001 | |
| WO | 98/42988 | 10/1998 | |
| WO | WO 9956676 A1 * | 11/1999 | ......... A61B 17/1604 |
| WO | 02/069817 | 9/2002 | |
| WO | 2004/017857 | 3/2004 | |
| WO | 2004/043278 | 5/2004 | |
| WO | 2007/092869 | 8/2007 | |
| WO | 2007/120903 | 10/2007 | |
| WO | 2008/034276 | 3/2008 | |
| WO | 2008/097216 | 8/2008 | |
| WO | 2008/106240 | 9/2008 | |
| WO | 2008/153732 | 12/2008 | |

OTHER PUBLICATIONS

Earl D. McBride, M.D., "The Journal of Bone and Joint Surgery", A Mortised Transfacet Bone Block for Lumbosacral Fusion, vol. 31-A, No. 2, Apr. 1949, ten pages.

* cited by examiner

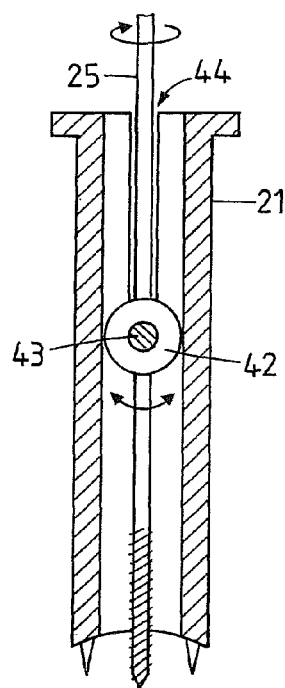
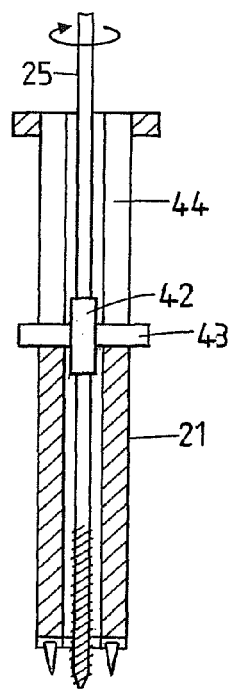
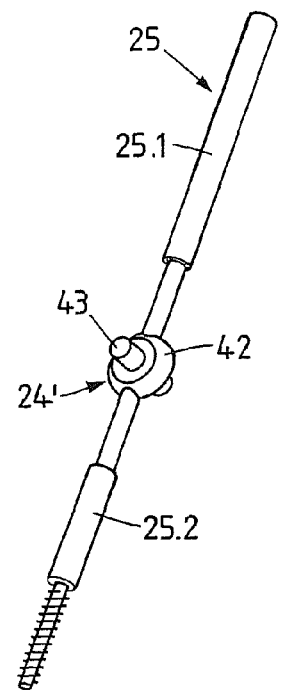
Fig. 6A     Fig. 6B     Fig. 6C
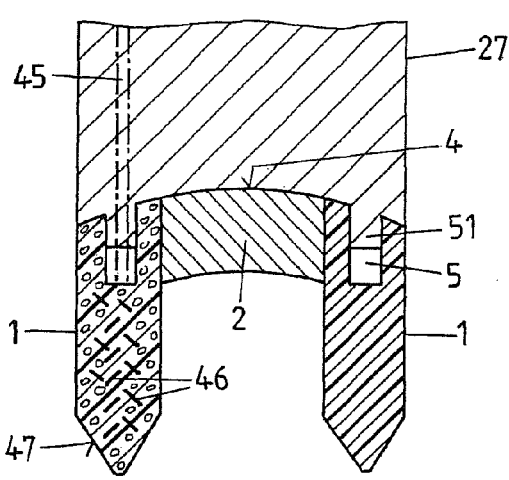
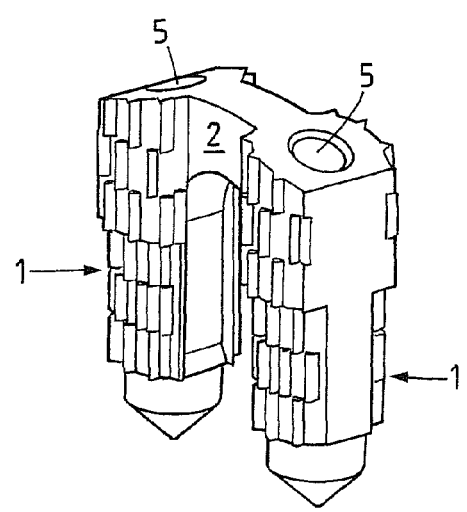
Fig. 7     Fig. 8

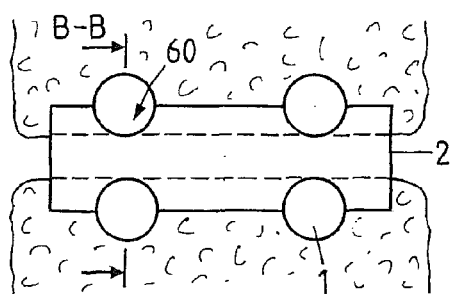
Fig. 13A
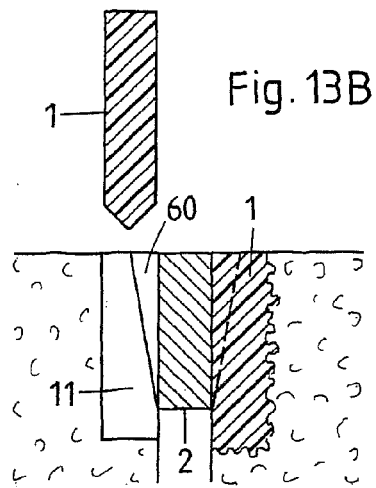
Fig. 13B
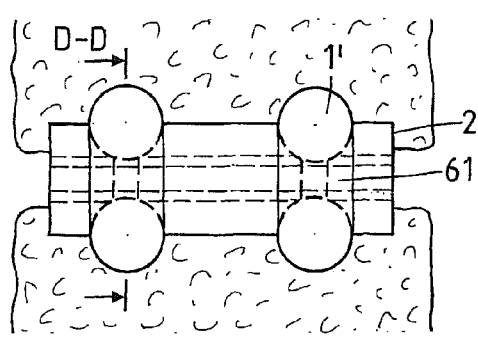
Fig. 13C
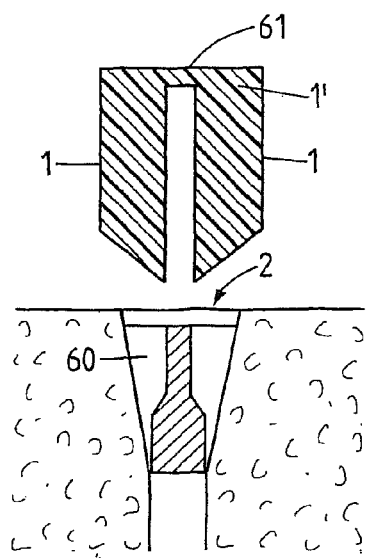
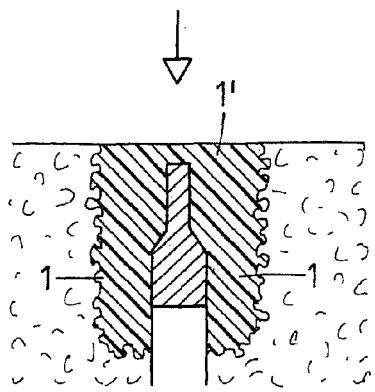
Fig. 13D

METHOD FOR FUSING A HUMAN OR ANIMAL JOINT AS WELL AS FUSION DEVICE AND TOOL SET FOR CARRYING OUT THE METHOD

BACKGROUND OF THE INVENTION

Field of the Invention

The invention is in the field of medical technology and concerns a method for fusing a human or animal joint (arthrodesis), wherein the joint is a synovial joint, i.e. an articulation between two bones each one comprising a cartilaginous articular surface, the movement of the articular surfaces relative to each other being lubricated by synovia which is confined in an articular capsule. The method is in particular suitable for fusing small synovial joints, such as human facet joints, joints of human hand and foot (including fingers and toes), sacroiliac joints, sternoclavicular joints, sternocostal articulations or costovertebral joints. The invention further concerns a fusion device and a tool set for carrying out the method.

Fusion of synovial joints serves e.g. as treatment for pain caused by degenerative or traumatic damage of the articular surfaces. The pain is relieved by preventing articular movement, i.e. by fixing the joint mechanically, usually followed by fusion of the originally articulating bones through osseoconduction (bone growth bridging the two articular surfaces). In the context of the present description the term "fusion" shall not only mean complete immobilization of the joint to be followed by osseoconduction (orthopedic indication), but, in particular when applied to a facet joint, also partial and/or temporal immobilization to stabilize a decompression procedure or for fixing a foramen distraction induced by flexion of the spine in a specific position (e.g. Mekka-position) of the patient or induced by application of distracting instruments (neurologic indication. Furthermore, such facet fusion may be used to allow spine fixation after milder correction of spinal curvature deformities or to support spine stabilization after correction of spondylotic conditions.

It has been known at least since 1949 ("A mortised transfacet bone block for lumbosacral fusion" by Earl D. McBride, Journal of Bone and Joint Surgery, volume 31-A, pp. 385-399, 1949) that fusion of the facet joints of lumbosacral vertebrae is a valid and simple way for immobilizing the concerned vertebrae relative to each other, in particular in connection with a disc operation. For fusing the facet joints McBride suggests transfacet bone blocks which are impacted under distraction into rectangular, undercut mortises having a depth of about 3 to 5 mm and extending from the laminae below to the facets above to form an interlaminar supporting strut.

Later authors propose fusion of facet joints through introduction of fusion devices between the articular surfaces of the joint, which fusion devices usually reach deeper (e.g. 10 to 20 mm) into the joint than the bone blocks described by McBride. Such fusion devices are e.g. block- or wedge-shaped elements or cages being introduced between the articular surfaces, or they are cylindrical or cone-shaped and are introduced in a corresponding bore extending substantially parallel to the articular surfaces, i.e. constituting two opposite grooves of which one extends in each one of the articular surfaces. In most cases it is suggested to decorticate the articular surfaces and to use fusion devices made of bone tissue or in the form of cages filled with bone material or bone replacement material such enhancing and accelerating the bone growth desired for full stabilization of the mechanically fused joint. In the time between the implantation of the fusion device and the achievement of full joint stabilization by a bony connection between the two bones, it is mainly friction which holds the fusion device in place and desirably reduces joint movement to a degree, which is high enough for enabling the desired bone growth. Most authors are of the opinion that for securing the position of the fusion device and for achieving the desired reduction in joint movement it is desirable or even necessary to oversize the fusion device for achieving a press-fit on implantation and/or to equip the fusion devices with locking means. Disclosed locking means range form flange-shaped extensions on the proximal side of block- or wedge-shaped elements or cages, which extensions are fixed to the dorsal or lateral surfaces of the articular processes (disclosed e.g. in US 2005/0124993, Chappuis), to retention flanges (disclosed e.g. in US 2006/0111782, Petersen), retention ridges or protrusions (US 2009/0036927, Vestgaarden), threads (disclosed e.g. in US 2006/0190081, Kraus, or WO 2007/120903, Blackstone), or longitudinal ridges arranged on more or less cylindrical fusion device surfaces to be in contact with the bone tissue of the articular surfaces and possibly serving for grooving these surfaces on introduction of the fusion device into the joint (disclosed e.g. in US 2006/0085068, Barry). Further known locking means are separate locking elements such as e.g. staples, or cables which are arranged to hold the two articular processes forming the facet joint together e.g. by being wound around outer process surfaces or by reaching through translaminar bores (disclosed e.g. in US 2006/0190081). Such separate locking elements can also be used for facet joint fusion by themselves, i.e. without the further above described fusion device being introduced between the articular surfaces.

Mechanical immobilization of a synovial joint by simply pushing a fusion device, e.g. a wedge shaped fusion device, between the articular surfaces is sufficient for joint fusion only if the articulating bones are biased against each other by an unyielding bone and/or cartilage structure as is the case e.g. for the facet joints and the sacroiliac joint and possibly for the sternocostal articulations or costovertebral joints. For fusion of synovial joints in which the articulating bones are connected only by ligaments, which relax under tension, sufficient mechanical immobilization is possible only with a fusion device which is firmly connected to the articular surfaces or which is combined with additional elements holding the articulating bones together. The latter is in particular the case for the joints of the human hand and foot (including fingers and toes) and for the sternoclavicular joints.

Methods and tool sets for facet joint fusion with the aid of a fusion device are described e.g. in the publications US 2009/0076551 (Petersen), US 2009/0036927 (Vestgaarden), WO 2008/097216 (Marino), WO 2007/120903 (Blackstone) and US 2006/0085068 (Barry).

It is the object of the invention to provide a method for fusing human or animal synovial joints, in particular for fusing small synovial joints such as human facet joints, joints of human hand and foot (including fingers and toes), sacroiliac joints, sternoclavicular joints, sternocostal articulations, or costovertebral joints. It is a further object of the invention to provide a fusion device and a tool set for carrying out the method. The improvement of the method and the fusion device according to the invention over known methods for the same purpose regards in particular the stability of the fusion device immediately after implantation, the enablement of bone growth by the implanted fusion device and/or the simplicity of the implantation procedure. This means that, after implantation, the fusion device according to the invention is to be able to remain in place and to immobilize the joint to a sufficiently high degree without the necessity of additional locking elements and, all the same and if so desired, the fusion device is to enable optimal osteoconduction between the two bones of the joint and preferably optimal osseointegration of the fusion device in the bone tissue, and, all the same, the implantation of the fusion device is to be simple and suitable for minimally invasive surgery.

These objects are achieved by the method, the fusion device, and the tool set as defined in the corresponding claims.

The following description concentrates in particular on fusion of human facet joints. This does not constitute a limitation of the teaching according to the invention to facet joint fusion, wherein the described method, fusion device and tool set is particularly suitable for fusion of the lumbar facet joints (L1/L2 to L5/S1). However, it is easily possible for one skilled in the art to adapt the disclosed method, as well as the forms and dimensions of the fusion device and of the tools, not only for application in other facet joints (in particular of the thoracic and cervical region) but also for applications regarding other synovial joints, in particular the synovial joints as mentioned in the first paragraph of the present description.

The method and the fusion device according to the invention are preferably based on the known implantation technique according to which an implant comprising a material having thermoplastic properties and being liquefiable by mechanical vibration is anchored in hard tissue, in particular in bone tissue, by applying such vibration to the implant, in particular ultrasonic vibration. These implantation techniques as well as implants being suitable for the implantation techniques are disclosed e.g. in the publications U.S. Pat. No. 7,335,205, U.S. Pat. No. 7,008,226, US 2006/0105295, and US-2008/109080 as well as in the US provisional applications U.S. 60/983,791, and U.S. 61/049, 587, which are not published yet. The disclosure of all the named publications and applications is enclosed herein by reference.

The basis of the above named implantation techniques is the in situ liquefaction of a thermoplastic material having mechanical properties suitable for a mechanically satisfactory anchorage of the fusion device in the bone tissue, wherein the material in its liquefied state has a viscosity which enables it to penetrate into natural or beforehand provided pores, cavities or other structures of the bone tissue, and wherein an only relatively small amount of the material is liquefied such that no unacceptable thermal load is put on the tissue. When re-solidified, the thermoplastic material which has penetrated into the pores, cavities or other structures constitutes a positive fit connection with the bone tissue.

Suitable liquefaction connected with an acceptable thermal loading of the tissue and giving suitable mechanical properties of the positive fit connections is achievable by using materials with thermoplastic properties having a modulus of elasticity of at least 0.5 GPa and a melting temperature of up to about 350° C. and by providing such material e.g. on an implant surface, which on implantation is pressed against the bone tissue, preferably by introducing the implant in a bone opening which is slightly smaller than the implant or by expanding the implant in a bone opening which originally is slightly larger than a implant (expansion e.g. by mechanically compressing or buckling the implant). During implantation, the implant is subjected to vibration of a frequency preferably in the range of between 2 and 200 kHz (preferably ultrasonic vibration) by applying e.g. the sonotrode of an ultrasonic device to the implant. Due to the relatively high modulus of elasticity the thermoplastic material transmits the ultrasonic vibration with such little damping that inner liquefaction and thus destabilization of the fusion device does not occur, i.e. liquefaction occurs only where the liquefiable material is in contact with the bone tissue and is therewith easily controllable and can be kept to a minimum.

Instead of providing the liquefiable material on the surface of the implant (disclosed e.g. in U.S. Pat. No. 7,335,205 or U.S. Pat. No. 7,008,226), it is possible also to provide the liquefiable material in a perforated sheath and to liquefy it within the sheath and press it through the sheath perforation to the surface of the fusion device and into the pores or cavities of the bone tissue (disclosed e.g. in U.S. Pat. No. 7,335,205, U.S. Pat. No. 7,008,226 and U.S. provisional application 61/049,5879) and/or it is possible to liquefy the liquefiable material between two implant parts of which one is vibrated and the other one serves as counter element, the interface between the two implant parts being positioned as near as possible to the bone tissue (as disclosed in the US provisional applications 60/983,791 and 61/049,587).

In specific embodiments of the method according to the invention, it is possible to exploit energy types other than vibrational energy for creating the local thermal energy needed for the liquefaction of the material with thermoplastic properties. Such other energy types are in particular rotational energy turned into friction heat in substantially the same manner as the vibrational energy, or electromagnetic radiation (in particular laser light in the visible or infrared frequency range), which radiation is preferably guided through the material with thermoplastic properties and locally absorbed by an absorber being contained in the material with thermoplastic properties or being arranged adjacent to this material. For specific embodiments of the fusion device and specific applications it may be possible to use other methods for anchoring the device in the joint than anchorage with the aid of a thermoplastic material which is liquefied to penetrate into the bone tissue. Such other methods are e.g. simple positioning of the device between the correspondingly prepared articular surfaces, wherein for retaining the device in the position in which it is implanted, the device is dimensioned for a press-fit and/or specific device parts comprise per se known retention means such as e.g. barbs, resilient protrusions, threads or cutting edges able to groove the bone tissue on implantation.

Preferred embodiments of the fusion device according to the invention comprise at least two device portions: at least one anchorage portion (preferably two) equipped for anchorage of the fusion device in the bone tissue using one of the above shortly described anchorage methods, and at least one stabilization portion which may be equipped for furthering osseointegration of the fusion device in the joint. These embodiments of the fusion device are preferably implanted essentially between the suitably prepared articular surfaces of the joint and the device portions are designed to delimit at least partly at least one osteoconduction region, i.e. a preferably central region in which the two articular surfaces face each other directly (without a device portion therebetween), and, if decorticated, at a small distance from each other.

According to the preferred embodiment of the method according to the invention, the above described preferred embodiment of the fusion device is pushed between the articular surfaces in an implantation direction. The fusion device has a depth in the implantation direction, which depth extends from a proximal device face being adapted for holding and guiding the fusion device with a tool during the implantation and for applying the vibration (or possibly other energy) to the fusion device, to a distal device end facing forward during the implantation. The fusion device further has a width (parallel to the articular surfaces) and a thickness or thickness profile (perpendicular to the articular surfaces), width and thickness extending perpendicular to the implantation direction. The fusion device portions (anchorage and stabilization portions) are arranged alternately beside each other in the direction of the device width, the anchorage portion(s) having a larger thickness and preferably a larger depth than the stabilization portion(s). The thickness difference between the anchorage portion(s) and the stabilization portion(s) amounts preferably to a few millimeters and grooves are provided in the articular surfaces for accommodation of the thicker anchorage portion(s).

The anchorage portion(s) has(have) preferably the form of a pin with a tapering distal end, the stabilization portion(s) has(have) preferably the form of a plate or wedge and is joined to a lateral side of the anchorage portion(s). Osteoconduction regions are delimited by concave device contours, i.e. by at least one lateral side of an anchorage portion and at least one distal or proximal face of at least one stabilization portion, and/or by at least one through opening in a stabilization portion.

The anchorage portion comprises the liquefiable material. The stabilization portion may also comprise a liquefiable material, which may be the same as or different from the liquefiable material of the anchorage portion, but may further comprise or consist of a non-liquefiable material (e.g. a metal), and it preferably comprises surfaces with a coating and/or surface structure which is suitable for enhancing osseointegration.

The overall depth and width of the fusion device is adapted to the size of the articular surfaces of the joint to be fused. Therein it is advantageous for the fusion device not to take up more than about half to about three quarters of the articular surfaces and that the osteoconduction regions amount to at least about a fifth of the articular surfaces. The thickness of the stabilization portion(s) is chosen to easily fit into the gap between the two articular surfaces, if applicable in their prepared state (after decortication or removal of cartilage).

There is no necessity for the fusion device according to the invention to comprise any bone or bone replacement material; however, it may of course do so. Bone growth enhancing material such as e.g. allograft or autograft bone material, bone replacement material, sponges, BMP carriers, if used, are preferably arranged in the osteoconduction region of the fusion device, wherein the named materials may be positioned between the prepared articular surfaces before positioning and anchoring the fusion device or wherein the named materials may be preassembled with the fusion device. For such preassembly, device surfaces of the concave device contour delimiting the osteoconduction region may carry retention means such as e.g. grooves or dents for retaining the named material.

The preferred embodiment of the method according to the invention comprises the following two steps:

Fixation step: fixation of the joint in a desired position, wherein the articular surfaces are positioned directly against each other (closed joint gap) or have a desired distance from each other (the fixation step is not necessary if the joint capsule is firm and taut enough for taking over the fixation function).

Preparation step: Removal of cartilage and possibly decortication of the articular surfaces, at least for preparation of grooves adapted to the anchorage portion(s) of the fusion device (removal of the cartilage from the entire articular surface is possible but not necessary; preparation of grooves is not necessary, if the anchorage portion(s) comprises self-reaming structures, i.e. is equipped as disclosed in US 2006/0105295, whose disclosure is incorporated herein by reference);

Implantation step: Introduction of the fusion device between the articular surfaces and application of energy, preferably mechanical vibration, to the fusion device either during introduction (if the liquefiable material is to be liquefied while being pressed against the bone tissue) or after introduction (if the liquefiable material is to be liquefied inside a perforated sheath and pressed through the sheath perforation and/or if the liquefiable material is liquefied between two device parts).

Finishing step: tools are separated from the fusion device and, if applicable, fixation of the joint is released.

The articular surfaces remain fixed relative to each other during the preparation step and the implantation step. This means that the fusion device is not meant to distract the joint and any desired relevant joint distraction has to be achieved with the aid of per se known means before the fixation step.

Further embodiments of the fusion device and the method according to the invention may vary from the above shortly described preferred embodiments in that:

Anchorage portions (preferably two) and stabilization portions (preferably one) of the fusion device constitute separate device parts (multi-part or preferably three-part fusion device as opposed to the above described one-part fusion device), wherein the anchorage portions are positioned and anchored between the articular surfaces in the joint first, and the stabilization portion is then mounted on the proximal ends of the anchorage portions, or wherein the stabilization portion is positioned between the articular surfaces first and the anchorage portions are then pushed through or past the stabilization portion and anchored in the bone tissue beside and/or beyond the stabilization portion (see FIGS. 12 to 14).

The fusion device does not comprise any stabilization portion, i.e. it comprises only one anchorage portion or a plurality of anchorage portions preferably being implanted simultaneously.

The liquefiable material is provided on one side of the anchorage portion(s) only such that the fusion device is anchored in one articular surface only. This may provide enough mechanical joint immobilization for joint fusion, in particular in the case of unyieldingly biased joints such as facet joints and sacroiliac joints. A similar one-sided anchorage can be achieved with anchorage portions comprising the liquefiable material all around, but by not removing the articular cartilage layer on the one articular surface and therewith rendering anchorage through the liquefiable material virtually impossible.

The fusion device comprises e.g. two anchorage portions and one stabilization portion constituting a one-part device or a three-part device and the fusion device is not implanted between the articular surfaces but is implanted such that the device width is oriented substantially perpendicular or at an oblique angle to the articular surfaces, the anchorage portions being anchored not in grooves prepared in the articular surfaces but in openings, e.g. bores in the bone tissue adjacent to the articular surfaces (see FIGS. 19 and 20).

BRIEF DESCRIPTION OF THE DRAWINGS

A plurality of exemplary embodiments of the method, the fusion device and the tool set according to the invention are illustrated in the following Figs., wherein:

FIGS. 6A to 6C show a preferred embodiment of a guide bush and a cutter for the tool set according to FIGS. 4A to 4H, wherein the cutter guide is integrated in the guide bush and the cutter;

FIG. 7 is a larger scale section through the fusion device according to FIGS. 1A to 1C, the fusion device being mounted on the distal end of the vibration tool;

FIG. 8 is a three-dimensional illustration of a fusion device similar to the one according to FIGS. 1A to 1C;

FIGS. 13A to 13D show two further embodiments of the fusion device according to the invention, which are based on the same principle as the device according to FIG. 12;

DETAILED DESCRIPTION OF THE INVENTION

Figure 1A:
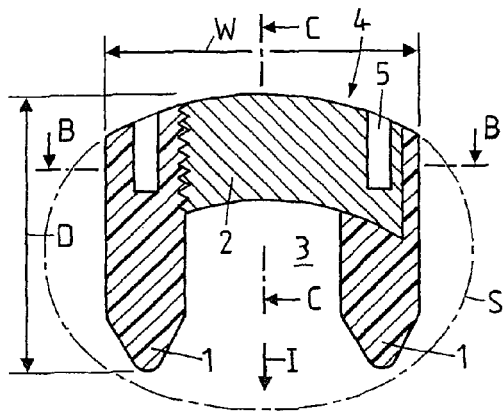
FIGS. 1A to 1C show different sections through a preferred embodiment of the fusion device according to the invention, the one-part fusion device comprising two anchorage portions and one stabilization portion arranged between the anchorage portions.
Figure 1B:
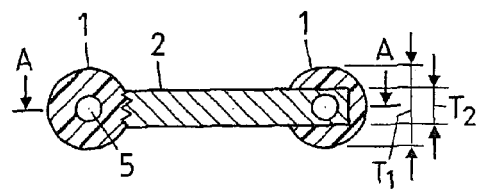
Figure 1C:
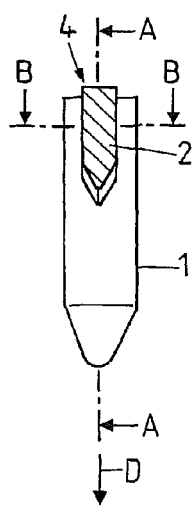

FIGS. 1A to 1C show a first exemplary embodiment of the fusion device according to the invention. The illustrated embodiment is particularly suited for fusion of a human lumbar facet joint, but, if correspondingly adapted, may also serve for fusion of other human facet joints or of other small synovial joints in a human or animal patient. FIG. 1A shows the fusion device in section perpendicular to its thickness (parallel to the implantation direction I; section line A-A in FIGS. 1B and 1C), FIG. 1B shows the fusion device in section perpendicular to its depth (implantation direction I perpendicular to the paper plane; section line B-B in FIGS. 1A and 1C), and FIG. 1C shows the fusion device in section perpendicular to is width (parallel to the implantation direction I; section line C-C in FIGS. 1A and 1B). FIG. 1A also shows very schematically, outlines of an articular surface (dash-dotted line S) and the position of the implanted fusion device in relation thereto.

The fusion device comprises two pin-shaped anchorage portions 1 and a stabilization portion 2 situated between the two anchorage portions 1. Distally, the anchorage portions 1 and the stabilization portion 2 form together a concave device contour which delimits an osteoconduction region 3. In this osteoconduction region 3 some bone growth furthering material may be positioned either before or after implantation of the device, wherein, for preassembly of the device and such material, device surfaces in the region of the named concave device contour may be equipped with spikes, barbs or other surface structures suitable for holding the bone growth furthering material. The fusion device has an overall depth D, an overall width W and a thickness profile comprising two general thicknesses (T1 of the anchorage portions 1 being larger than T2 of the stabilization portion 2).

The stabilization portion 2 is e.g. made of a non-liquefiable (in the sense of the anchoring technique) material, e.g. of a metal (e.g. titanium or titanium alloy), of a ceramic material (e.g. zirconium oxide) or of a thermoset polymer or thermoplastic polymer (e.g. PEEK) having a melting temperature, which is sufficiently higher than the melting temperature of the liquefiable material. The stabilization portion may also be made of a composite material comprising e.g. a trabecular metal (e.g. titanium or tantalum) and a thermoset or thermoplastic polymer. The composite material comprising endless fibers (e.g. carbon fibers) molded into a plastic material (e.g. PEEK OPTIMA Polymer™) with the aid of the composite flow molding process by the Swiss firm "icotec" is a further suitable material for the stabilization portion. Non-resorbable polymeric or composite materials used for the stabilization portion are preferably equipped with osseointegration supporting means like e.g. a coating of hydroxy apatite.

The anchorage portions 1 comprise the liquefiable material at least on their surfaces to come into contact with the bone tissue or are e.g. made of this material, wherein, if the anchorage is to be achieved with the aid of mechanical vibration, the named surfaces preferably comprise energy directors (not shown) e.g. in the form of protruding humps or axial ridges. The anchorage portions 1 are joined to the stabilization portion 2 by adhesion or, as illustrated on the left hand side of the fusion device of FIG. 1A, via a rough surface or surface structure suitable for forming together with the liquefiable material a positive fit connection. For a stronger connection between the anchorage portions 1 and the stabilization portion 2 the latter may reach into or through the anchorage portions 1 as illustrated on the right hand side of the fusion device of FIG. 1A. The fusion device is manufactured by e.g. positioning the stabilization portion 2 into a corresponding mould and injection-molding the anchorage portions 1 to or around the stabilization portion 2.

The fusion device embodiment as illustrated in FIGS. 1A to 1C may further comprise a bridge or edge portion (not shown) connecting the two proximal ends of the anchorage portions 1 and covering the proximal face and possibly up to about 20% of the depth of the stabilization portion and consisting of the liquefiable material. Such a bridge or edge portion of an implanted fusion device constitutes a polymer seam tightly closing the joint gap. In a further embodiment of the fusion device similar to the one shown in FIGS. 1A to 1C the stabilization portion as well as the anchorage portions are made entirely of the liquefiable material (see also FIG. 8).

Figure 4:
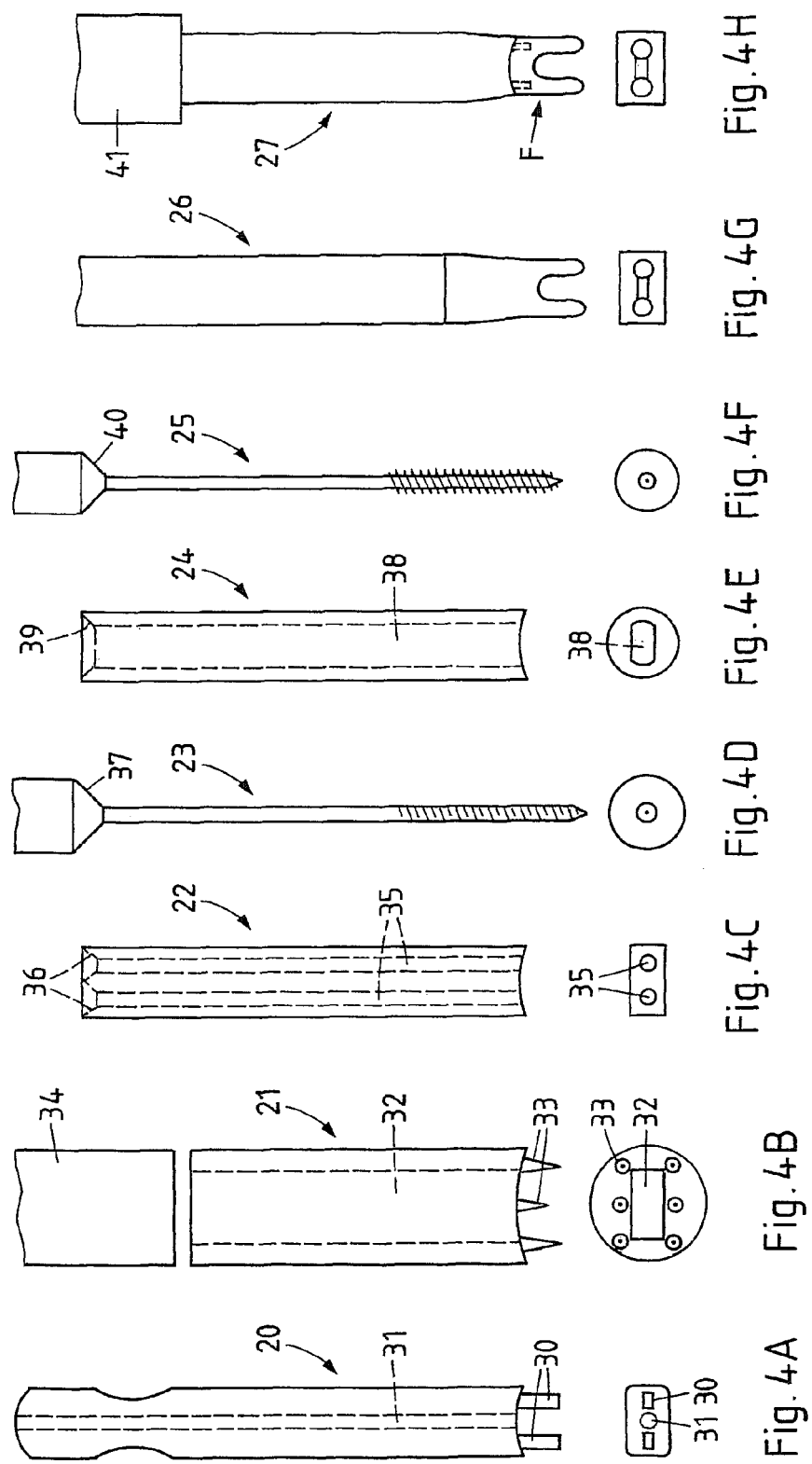
FIGS. 4A to 4H show eight tools of an exemplary embodiment of the tool set according to the invention, each tool being illustrated viewed from the side and towards the distal tool end, the tool set being suitable for implantation of the fusion device according to FIGS. 1A to 1C with the method as illustrated in FIGS. 2A to 2D.

The proximal face 4 of the fusion device is preferably adapted to a rim portion of the articular surfaces by being curved. Preferably the proximal face 4 comprises means for the fusion device to be held by a tool, e.g. by a vibration tool. Such means are e.g. axial openings or bores 5 arranged e.g. in the region of the anchorage portions 1 and cooperating with corresponding protrusions provided on a distal tool face (see also FIG. 4).

The two thicknesses T1 and T2 are e.g. in the range of 1 to 3 mm and 3 to 8 mm. If the fusion device is to be used for fusing a human facet joint, its overall depth is in the range of 5 to 20 mm, preferably 7 to 20 mm, its overall width in the range of 5 to 20 mm, preferably 5 to 15 mm.

Suitable liquefiable materials to be used for the anchorage portions 1 and possibly for part of the stabilization portion (bridge portion) or the whole stabilization portion are thermoplastic polymers, e.g.: resorbable polymers such as polymers based on lactic and/or glycolic acid (PLA, PLLA, PGA, PLGA etc.) or polyhydroxy alkanoates (PHA), polycaprolactone (PCL), polysaccharides, polydioxanes (PD) polyanhydrides, polypeptides or corresponding copolymers or composite materials containing the named polymers as a component; or non-resorbable polymers such as polyolefines (e.g. polyethylene), polyacrylates, polymetacrylates, polycarbonates, polyamides, polyester, polyurethanes, polysulfones, polyarylketones, polyimides, polyphenylsulfides or liquid crystal polymers LCPs, polyacetales, halogenated polymers, in particular halogenated polyolefines, polyphenylensulfides, polysulfones, polyethers or equivalent copolymers or composite materials containing the named polymers as a component.

Specific embodiments of degradable materials are Polylactides like LR706 PLDLLA 70/30, R208 PLDLA 50/50, L210S, and PLLA 100% L, all of Böhringer. A list of suitable degradable polymer materials can also be found in: Erich Wintermantel und Suk-Woo Haa, "Medizinaltechnik mit biokompatiblen Materialien und Verfahren", 3. Auflage, Springer, Berlin 2002 (in the following referred to as "Wintermantel"), page 200; for information on PGA and PLA see pages 202 ff., on PCL see page 207, on PHB/PHV copolymers page 206; on polydioxanone PDS page 209. Discussion of a further bioresorbable material can for example be found in CA Bailey et al., J Hand Surg [Br] 2006 April; 31(2):208-12.

Specific embodiments of non-degradable materials are: Polyetherketone (PEEK Optima, Grades 450 and 150, Invibio Ltd), Polyetherimide, Polyamide 12, Polyamide 11, Polyamide 6, Polyamide 66, Polycarbonate, Polymethylmethacrylate, Polyoxymethylene. An overview table of polymers and applications is listed in Wintermantel, page 150; specific examples can be found in Wintermantel page 161 ff. (PE, Hostalen Gur 812, Höchst AG), pages 164 ff. (PET) 169 ff. (PA, namely PA 6 and PA 66), 171 ff. (PTFE), 173 ff. (PMMA), 180 (PUR, see table), 186 ff. (PEEK), 189 ff. (PSU), 191 ff (POM—Polyacetal, tradenames Delrin, Tenac, has also been used in endoprostheses by Protec).

The liquefiable material having thermoplastic properties may contain foreign phases or compounds serving further functions. In particular, the thermoplastic material may be strengthened by admixed fibers or whiskers (e.g. of calcium phosphate ceramics or glasses) and such represent a composite material. The thermoplastic material may further contain components which expand or dissolve (create pores) in situ (e.g. polyesters, polysaccharides, hydrogels, sodium phosphates), compounds which render the fusion device opaque and therewith visible for X-ray, or compounds to be released in situ and having a therapeutic effect, e.g. promotion of healing and regeneration (e.g. growth factors, antibiotics, inflammation inhibitors or buffers such as sodium phosphate or calcium carbonate against adverse effects of acidic decomposition). If the thermoplastic material is resorbable, release of such compounds is delayed. If the device is to be anchored not with the aid of vibration energy but with the aid of electromagnetic radiation, the liquefiable material having thermoplastic properties may locally contain compounds (particulate or molecular) which are capable of absorbing such radiation of a specific frequency range (in particular of the visible or infrared frequency range), e.g. calcium phosphates, calcium carbonates, sodium phosphates, titanium oxide, mica, saturated fatty acids, polysaccharides, glucose or mixtures thereof.

Fillers used may include degradable, osseostimulative fillers to be used in degradable polymers, including: β-Tricalciumphosphate (TCP), Hydroxyapatite (HA, <90% crystallinity; or mixtures of TCP, HA, DHCP, Bioglasses (see Wintermantel). Osseo-integration stimulating fillers that are only partially or hardly degradable, for non degradable polymers include: Bioglasses, Hydroxyapatite (>90% cristallinity), HAPEX®, see S M Rea et al., J Mater Sci Mater Med. 2004 September; 15(9):997-1005; for hydroxyapatite see also L. Fang et al., Biomaterials 2006 July; 27(20):3701-7, M. Huang et al., J Mater Sci Mater Med 2003 July; 14(7):655-60, and W. Bonfield and E. Tanner, Materials World 1997 January; 5 no. 1:18-20. Embodiments of bioactive fillers and their discussion can for example be found in X. Huang and X. Miao, J Biomater App. 2007 April; 21(4):351-74), JA Juhasz et al. Biomaterials, 2004 March; 25(6):949-55. Particulate filler types include: coarse type: 5-20 μm (contents, preferentially 10-25% by volume), submicron (nanofillers as from precipitation, preferentially plate like aspect ratio >10, 10-50 nm, contents 0.5 to 5% by volume).

Figure 2A:
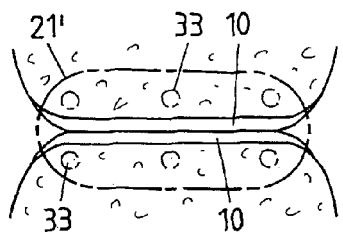
FIGS. 2A to 2D show four successive phases of a preferred embodiment of the method according to the invention, wherein the fusion device according to FIGS. 1A to 1C is implanted between the articular surfaces of e.g. a human facet joint.
Figure 2B:
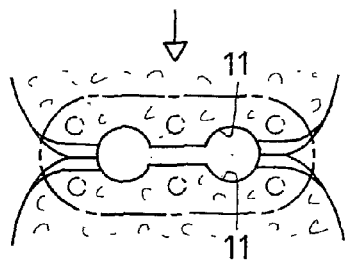

FIGS. 2A to 2D, as exemplary embodiment of the method according to the invention, illustrate the implantation of a fusion device similar to the one shown in FIGS. 1A to 1C in a joint, e.g. in a human facet joint, whose articular surfaces are but slightly convex/concave, wherein anchorage of the anchorage portions of the device is achieved with the aid of mechanical vibration. FIG. 2A shows in section perpendicular to the implantation direction the articular surfaces of the joint. These articular surfaces are, at least in a healthy and undamaged state, fully coated with articular cartilage 10.

In a fixation step the articular surfaces of the facet joint are fixed relative to each other e.g. by positioning a guide tool against a posterior or lateral surface of the articular processes, such that the distal tool face 21' reaches across the joint gap, and forcing spikes 33 arranged on this distal tool face 21' into the process bone on both sides of the joint gap.

If, in the fixation step, a gap between the articular surfaces being wider than the natural gap is to be fixed, a corresponding distractor tool (not illustrated in FIGS. 2A to 2D) is introduced in the gap before positioning the guide tool, or the vertebral column of the patient is brought into a correspondingly bent position.

In the preparation step being carried out after the fixation step, two bores are drilled substantially parallel to the articular surfaces and parallel to each other, the bores constituting the grooves 11 in the articular surfaces and serving for accommodating the anchorage portions of the fusion device. The bores preferably have a diameter being sufficiently large for the cartilage layer and at least part of the cortical bone beneath the cartilage layer to be grooved. Furthermore, it is preferable to also remove the cartilage layer and possibly some cortical bone between the two bores, to a depth which is at least as large as the depth of the stabilization portion of the fusion device and preferably as large as the overall depth of the fusion device (including the osteoconduction region). Depending on the anchorage technique, the diameter of the bores may need to be slightly smaller than the diameter of the anchorage portions. If the stabilization portion also comprises liquefiable material the thickness of the stabilization portion may be adapted to the gap between the possibly prepared articular surfaces such that the stabilization portion can be introduced into this gap without substantial friction, i.e. such that virtually no liquefaction occurs, or such that on introduction under vibration the stabilization portion is anchored in the articular surfaces substantially in the same manner as the anchoring portions. The space between the articular surfaces created in the preparation step (FIG. 2B) is optionally at least partially filled with a material capable of furthering bone growth (e.g. bone paste or bone replacement material) in order to improve osteoconduction between the two articular surfaces and possibly osseointegration of the fusion device.

Figure 2C:
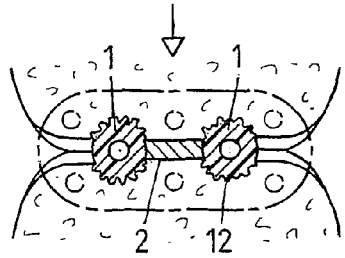

In the implantation step, the fusion device is inserted between the prepared articular surfaces with the anchorage portions being introduced into the bores and the fusion device is simultaneously vibrated with the aid of a vibration tool which is applied to the proximal face of the fusion device (FIG. 2C). Due to the contact of surfaces of the vibrating fusion device with the non-vibrating bone tissue at least in the region of the grooves 11, the liquefiable material provided on these device surfaces is liquefied and penetrates into the bone tissue, where, after solidification, it constitutes a positive fit connection between the bone tissue and the fusion device, in particular the anchorage portions thereof (illustrated by squiggly lines 12 in FIG. 2C).

Figure 2D:
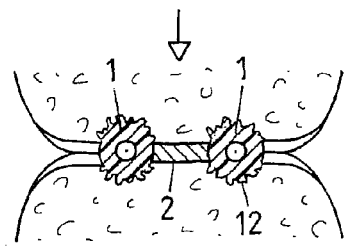

After positioning and anchoring the fusion device in the joint, the tool used for the anchorage is separated from the fusion device and the joint fixation is released (finishing step, e.g. removal of guide tool) as shown in FIG. 2D. Obviously the anchored fusion device as shown in FIG. 2D is securely kept in its position and prevents not only articulation of the joint but also movements due to shearing forces in all directions, due to torque, and due to bending forces in planes other than articulating planes. However, due to the relatively low modulus of elasticity of the thermoplastic material constituting the anchorage, the positive fit connection between the fusion device and the bone tissue of the fused joint still allows very small movements of the two bones relative to each other, which micro movements are known to enhance osseointegration and osteoconduction.

Figure 3:
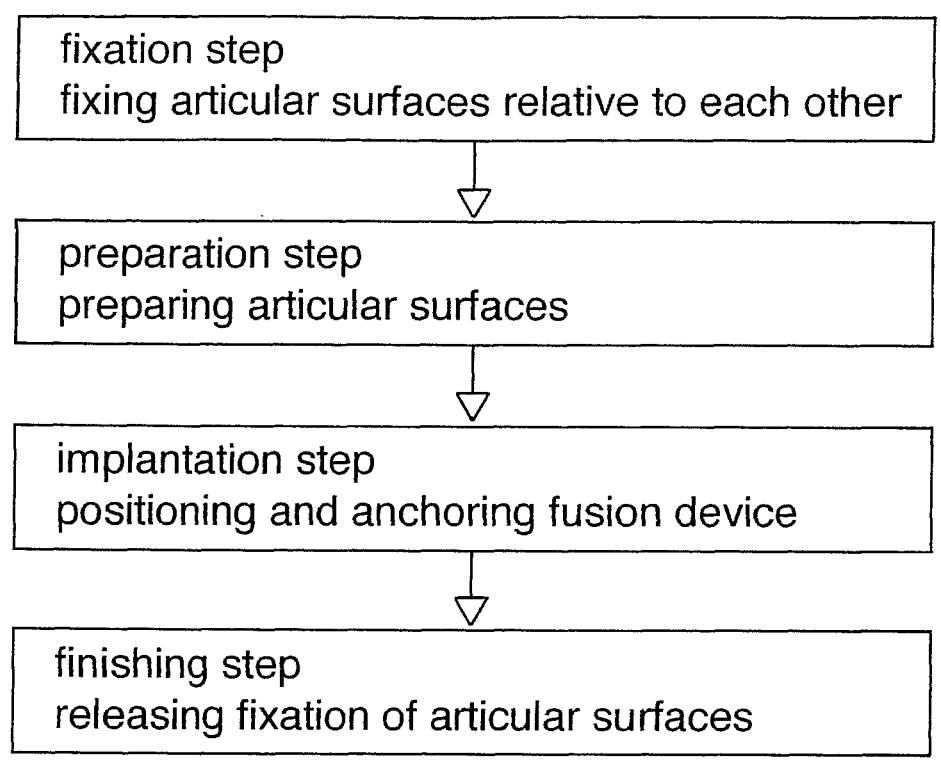
FIG. 3 is a flow chart for the method as illustrated in FIGS. 2A to 2D.

FIG. 3 is a flow chart of the method as illustrated in FIGS. 2A to 2D and shows the fixation step, the preparation step, the implantation step and the finishing step. If fixation of the joint by the joint capsule is sufficient, the fixing step and the finishing step are not necessary. The preparation step is not a necessary step (see further below), i.e. the implantation step may be carried out immediately after the fixation step. In any case, some preparation (e.g. decortication of a larger area of the articular surfaces) may be carried out before the fixation step.

FIGS. 4A to 4H show the tools of an exemplary embodiment of the tool set according to the invention, the tool set serving for carrying out the method according to the invention. The tool set is e.g. suitable for implanting a fusion device as illustrated in FIGS. 1A to 1C in a method, whose main steps are illustrated in FIGS. 2A to 2D and in FIG. 3. Each tool of the tool set is shown viewed from the side and against the distal tool end. The tools, which are shown in the sequence of their use in the implantation method are the following: a gap finder 20 (FIG. 4A), a guide bush 21 (FIG. 4B), a drill guide 22 (FIG. 4C), a drill 23 (FIG. 4D), a cutter guide 24 (FIG. 4E), a cutter 25 (FIG. 4F), a control tool 26 (FIG. 4G), and a vibration tool 27 (FIG. 4H). Tools 20 and 21 are applicable in the fixation step, tools 22 to 26 in the preparation step, and tool 27 in the implantation step.

The gap finder 20 is equipped for finding and possibly distracting the gap between the two articular surfaces between which the fusion device is to be introduced and for marking the orientation of this gap. For this purpose it carries on its distal end at least one flat and blunt protrusion (e.g. two protrusions 30) which is suitable for being pushed between the articular surfaces and possibly for temporarily keeping them at a predetermined distance from each other. Depending on the form of the articular surfaces of the joint to be fused, the protrusions 30 of the gap finder 20 may not extend fully axially as illustrated but may be slightly bent (in the range of about 10°) away from the axial direction, which e.g. for introduction into a facet joint is advantageous. The gap finder 20 may further comprise an axial bore 31 for accommodating a K-wire (not shown) being used for locating the gap between the articular surfaces to start with, and for guiding the gap finder 20 towards the gap, wherein the gap finder 20 is pushed along the wire. The gap finder 20 has a cross section with one distinguished larger diameter in the direction of the gap being located with the aid of the distal protrusions or the direction defined by the protrusions respectively (the cross section is e.g. oblong as illustrated or oval but not circular nor square), this cross section being adapted to the fusion device as well as to inner or outer cross sections of the further tools of the tool set in a way to be elaborated further down.

The guide bush 21 comprises an axial tunnel 32 for guiding the guide bush 21 along the gap finder 20, i.e. the tunnel has a cross section which corresponds to the cross section of the gap finder 20. As already discussed in connection with FIGS. 2A to 2D, the guide bush 21 carries on its distal end face a plurality of short and sharp spikes 33 or blades suitable for fixing the guide bush to the bone on either side of the articular surfaces and at the same time for fixing the articular surfaces relative to each other. The spikes are forced into the bone tissue e.g. by applying a punch 34 to its proximal end. The drill guide 22 comprises two axial bores 35 adapted in diameter and distance from each other to the diameter and the position of the anchorage portions of the fusion device. The outer cross section of the drill guide 22 is adapted to the cross section of the axial tunnel 32 of the guide bush 21 such that guidance of the drill guide 22 in this axial tunnel positions the drill guide 22 exactly over the gap between the articular surfaces. The drill guide 22 further comprises a stop shoulder 36, e.g. at its proximal end or inside the axial bores.

The drill 23 being equipped for drilling cartilage and bone tissue has a diameter being adapted to the diameter of the axial bores 35 of the drill guide 22 and an axial length from a distal end to a depth stop, e.g. a region of increasing diameter 37, which axial length is greater than the axial length of the drill guide from a distal end to the stop shoulder 36 by about the depth to which the fusion device is to be introduced between the articular surfaces.

The cutter guide 24 has substantially the same outer cross section as the drill guide 22 and comprises an axial tunnel 38 which has an oblong cross section being adapted to the proximal face of the stabilization portion of the fusion device. The cutter guide 24 further comprises a stop shoulder 39, e.g. on its proximal end as illustrated or inside the axial tunnel 38.

The cutter 25 is preferably a rotating tool equipped for removing cartilage and possibly bone tissue from between the two bores produced with the aid of the drill guide 22 and the drill 23. The cutter 25 is e.g. a drill having a cross section adapted to the smaller extension of the cross section of tunnel 38 and preferably being mounted to a rotational drive such that it can be laterally displaced or pivoted relative to a housing of the drive in the plane of the longer extension of the cross section of tunnel 38 in a very limited manner. The cutter may also be designed as a correspondingly shaped punching tool being e.g. driven by ultrasonic vibration. Such punching tools are disclosed in the publication US 2008/269649, the disclosure of which is enclosed herein by reference. The cutter 25 further comprises a depth stop 40 cooperating with the stop shoulder 39 of the cutter guide 24. The axial length of the cutter 25 from its distal end to the depth stop 40 is larger than the axial length of the cutter guide 24 from its distal end to the stop shoulder 39 by the depth to which the tissue between the two bores is to be removed, preferably at least by the depth of the stabilization portion of the fusion device.

The control tool 26 has a distal end similar to the vibration tool 27 carrying the fusion device (see below) but slightly undersized and adjoining this distal end it has a cross section which is the same as the outer cross section of drill guide and cutter guide. The control tool 26 advantageously carries depth marks (not shown) where it protrudes from the guide bush 21, the marks indicating depths to which the distal end of the control tool is introduced in the gap between the articular surfaces.

The vibration tool 27 is e.g. a sonotrode which is equipped for being coupled to a vibration drive, e.g. of an ultrasonic device. The distal end of the vibration tool 27 is equipped for holding the fusion device F and for transmitting vibration to the fusion device. For the latter function it is preferable for the distal face of the vibration tool 27 to be adapted exactly to the proximal face of the fusion device, e.g. by comprising a concave curvature corresponding exactly with the convex curvature of the proximal face of the fusion device F. In an area between the distal end and the proximal end the vibration tool has a cross section which is substantially the same as the outer cross section of the gap finder 20, of the drill guide 22, of the cutter guide 24 and of the control tool 26. The vibration tool 27 may comprise a depth stop 41 like the drill 23 and the cutter 25, which depth stop 41 cooperates e.g. with the proximal face of the guide bush 21 or with a corresponding stop shoulder inside the axial tunnel 32 of the guide bush. For giving the surgeon more freedom regarding implantation depth it may be advantageous to not equip the vibration tool 27 with a depth stop, but rather with one or a plurality of depth marks (not shown) which show the surgeon how deep the fusion device is introduced in the joint at any moment during implantation.

It is also possible to design the combination of vibration tool 27, fusion device F and guide bush 21 or part thereof as a load frame containing a biased spring which is released for the implantation step to provide the axial force and stroke necessary for the implantation step. Suitable such load frames are disclosed in the U.S. application No. 61/033,066, the disclosure of which is enclosed herein by reference.

Figure 5:
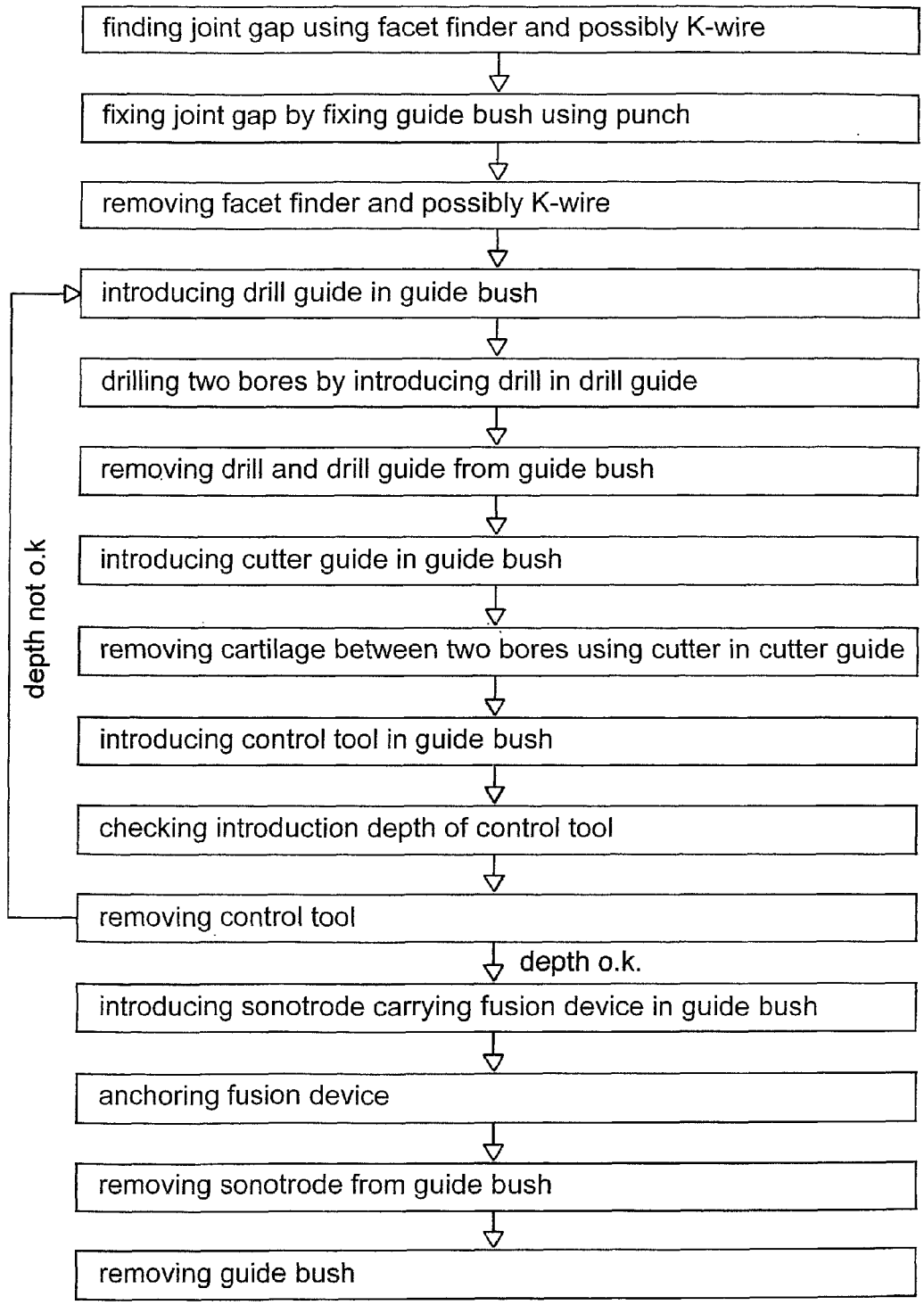
FIG. 5 is a flow chart of a method in which the whole tool set according to FIGS. 4A to 4H are used.

Implantation of the fusion device according to FIGS. 1A to 1C in a preferably minimally invasive or mini-open procedure with the aid of the tool set according to FIGS. 4A to 4H comprises the following steps, which are schematically illustrated in the flow diagram of FIG. 5:

Finding and marking the gap between the articular surfaces by positioning the protrusions 30 of the gap finder 20 in the gap, wherein the gap finder 20 is possibly introduced along a previously positioned K-wire.

Positioning and fixing the guide bush 21 on the bone surface on both sides of the gap by introducing the gap finder 20 into the axial tunnel 32 of the guide bush 21, by pushing the guide bush 21 against the bone until it abuts the bone surface, and by punching the spikes 33 or blades of the guide bush 21 into the bone surface using the punch 34.

Removing the gap finder 20.

Positioning the drill guide 22 in the axial tunnel 32 of the guide bush 21, making sure that its distal face abuts on the bone surface.

Positioning the drill 23 in one of the axial bores 35 of the drill guide 22, drilling the first bore and repeating positioning and drilling for the second bore, wherein the predefined depth of the bores is reached when the depth stop 37 of the drill 23 abuts on the stop shoulder 36 of the drill guide 22.

Removing the drill 23 and the drill guide 22 from the guide bush 21.

Positioning the cutter guide 24 into the axial tunnel 32 of the guide bush 21 making sure that its distal face abuts on the bone surface.

Positioning the cutter 25 into the axial tunnel 38 of the cutter guide 24 and activating it and, if applicable, moving it laterally in the axial tunnel 38 of the cutter guide 24, wherein the predefined depth of the tissue removal by cutting is reached when the depth stop 40 of the cutter 25 abuts on the stop shoulder 39 of the cutter guide.

Removing the cutter 25 and the cutter guide 24 from the guide bush 21.

Controlling the accuracy of the preparation of the joint by introducing the control tool 26 into the axial tunnel of the guide bush 21 and checking the introduction depth and removing the control tool.

If the controlled introduction depth is not o.k., repeating the steps of introducing the drill guide 22, of introducing the drill 23 and of drilling, the steps of introducing the cutter guide 24, of introducing the cutter 25 and of tissue removal, and the steps of introducing the control tool 26 and of checking the introduction depth.

If the controlled introduction depth is o.k., introducing the vibration tool 27 with the fusion device F mounted to its distal end into the axial tunnel 32 of the guide bush 21 and vibrating the tool 27 and therewith the fusion device F while introducing the fusion device into the space prepared in the steps of drilling and cutting between the articular surfaces, wherein a predetermined depth of introduction is reached when the depth stop 41 of the vibration tool 27 abuts on the proximal surface of the guide bush 21 or a freely selectable introduction depth is reached when a corresponding mark on the vibration tool has reached the proximal face of the guide bush 21.

Separating the vibration tool 27 from the anchored fusion device F and removing it from the guide bush 21.

Removing the guide bush 21.

The step of controlling the joint preparation using the control tool is not an obligatory step.

In a preferred tool set, the tools have the following further features, which may cooperate with further tools: For x-ray control of the correct position of its distal protrusions in the joint gap, the facet finder 20 (except for its distal protrusions) should have a sufficient transparency for x-rays through its length and at the same time needs a sufficient mechanical stiffness. Therefore it is proposed to e.g. manufacture the facet finder 20 of PEEK and to increase its transparency by providing a plurality of through openings along its length, or to manufacture it as a sandwich construction with two relatively thin rigid surface layers (e.g. made from carbon or glass fiber reinforced laminates) oriented parallel to the longer extension of the cross section and a center layer of foamed material (e.g. polyurethane foam) for better transparency. The guide bush 21 is designed to have a first axial length and in the region of its proximal end it comprises means for removeably fixing a laterally extending handle piece. The facet finder 20 has an axial length which is greater than the first axial length and it comprises a through opening situated beyond the proximal face of the guide bush 21 when the facet finder 20 is positioned in the guide bush. For removing the facet finder 20 from the guide bush 21, the distal end of an angled remover tool (not illustrated) is introduced into the through opening and is pivoted upwards while the remover tool is supported on the proximal face of the guide bush 21. The punch 34 has an axial channel of the same cross section as the axial channel of the guide bush 22 and an axial length such that the guide bush 21 and the punch 34 together have and axial length which is larger than the axial length of the facet finder 20 such that the punch 34 can be positioned over the proximal end of the facet finder being positioned in the guide bush 21. The drill guide 22 and the cutter guide 24 have proximal flanges which rest on the proximal face of the guide bush 21 when the distal end is positioned against the bone surface.

FIGS. 6A to 6C illustrate a preferred embodiment of guide bush 21, cutter guide 24', and cutter 25, which are operable for removing tissue between the two bores drilled with the aid of the drill guide and the drill. FIGS. 6A and 6B show the cutter guide 24' and the cutter 25 positioned in the guide bush 21, wherein FIG. 6A is an axial section parallel to the longer extension of the inner cross section of the guide bush and FIG. 6B an axial section parallel to the shorter extension of the cross section of the guide bush. FIG. 6C is a three-dimensional illustration of the assembly of cutter 25 and cutter guide 24'. In this embodiment, the cutter guide 24' comprises a disk 42 with two bolts 43 arranged to extend coaxially to the disk on both sides thereof and the guide bush 21 comprises two opposite slots 44, the slots 44 reaching distally from the proximal face of the guide bush. The disk 42 comprises a radial bore through which the cutter shaft extends being capable to move longitudinally and to be rotated relative to the disk 42. The disk 42 has a diameter which is adapted to the longer extension of the inner cross section of the guide bush 21 and a thickness which is adapted to the smaller extension of the inner cross section of the guide bush 21. The axial bolts 43 have a cross section which is adapted to the width of the slots 44. The cutter 25 with the disk 42 loosely arranged thereon (e.g. loosely held in place between two thicker portions 25.1 and 25.2 of the cutter shaft (FIG. 6C)), is introduced into the guide bush 21, the disk 42 guiding the cutter 25 in the axial channel of the guide bush 21 and the bolts 43 sliding along the slots 44 until they come to rest on the rounded ends of these slots. In this position of the disk, the cutter is capable of moving longitudinally between two positions defined by the thicker portions 25.1 and 25.2 and to be rotated. Furthermore, it is capable of being pivoted, the bolts 43 and the ends of slots 44 serving as pivot bearing, the disk 42 serving as centering guide and the guide bush 21 limiting the pivotal movement of the cutter 25. The removal of tissue is preferably finished, when the cutter 25 has reached its most distal position relative to the disk 42.

FIG. 7 is an axial section on a larger scale than FIG. 4H of the distal end of the vibration tool 27 and a fusion device similar to the one illustrated in FIGS. 1A to 1C being mounted thereon for implantation. The fusion device is held on the distal tool end by protrusions 51 extending from the distal tool face and being adapted to enter the openings 5 in the proximal face 4 of the fusion device. As already mentioned further above, for optimal transfer of the vibration to the fusion device and therewith optimal anchorage of the fusion device in the bone tissue it is preferable that the form of the distal tool face matches the form of the proximal face 4 of the fusion device as exactly as possible, such enabling transfer of the vibration from the tool 26 to the fusion device over the whole distal tool face.

The fusion device according to FIGS. 1A to 1C and 7, the implantation method according to FIGS. 2A to 2D, 3 and 5 and the tool set according to FIGS. 4A to 4H can be modified in e.g. the following manner, without departing from the basic idea of the invention:

The stabilization portion 2 of the fusion device is bent or bendable to be not straight and non-parallel to the device width W, the fusion device therewith being adapted or adaptable to fit more convex/concave articular surfaces (necessitates corresponding adaptation of the drill guide 22, the cutter guide 24, the control tool 26 and the vibration tool 27, and possibly of the gap finder 20 such that the protrusions 30 define a curved line instead of a straight line);

Both the anchorage portions 1 and the stabilization portion 2 of the fusion device are substantially made of a liquefiable material (see FIG. 8), wherein the device portions may be made of the same liquefiable material or different such materials, and wherein the stabilization portion 2 may carry a coating of a material which is capable of enhancing osseointegration. Such coating may e.g. comprise calcium phosphate or apatite;

Both the anchorage portions 1 and the stabilization portion 2 are made substantially of a non-liquefiable material, e.g. of titanium or a titanium alloy or of a ceramic material. The non-liquefiable material is preferably treated to have a surface structure, which in the region of the stabilization portion 2 enhances osseointegration and which in the region of the anchorage portions 1 is suitable for adherence of an at least partial coating comprising the liquefiable material. Anchorage portions comprising a metal core have the advantage of being visible with X-ray and therewith facilitating implantation. Such cores may also be removable after implantation.

The anchorage portions 1 have non-round cross sections (may necessitate adaptation of the drill guide 22 and possibly of the drill 23, which may be replaced by e.g. a vibration driven punching tool as disclosed in the publication US 2008/269649).

The proximal device face is not adapted to a curved rim of an articular surface but is e.g. straight and extending e.g. perpendicular to the implantation direction (necessitates corresponding adaptation of the distal face of the vibration tool 27).

The proximal face of the anchorage portions 1 does not comprise openings 5 adapted to corresponding protrusions 51 of the vibration tool 27 but vice versa or this proximal face is even. Further means and ways for attaching the fusion device to the distal end of the vibration tool are disclosed in the above named publications U.S. Pat. No. 7,335,205 and U.S. Pat. No. 7,008,226.

The distal regions of the anchorage portions 1 and/or of the stabilization portion 2 are not tapering or the anchorage portions 1 and/or the stabilization portion 2 taper continuously or in steps over their whole depth, i.e. from the proximal face to their distal end (necessitates corresponding adaptation of the drill 23 and possibly of the drill guide 22).

The difference in thickness between the anchorage portions 1 and the stabilization portion 2 is small (<1 mm) and/or the anchorage portions are equipped with self-reaming structures, such enabling implantation without the necessity of providing grooves 11 (use of the drill guide 22 and the drill 23 may be eliminated).

In the preparation step, larger portions of the articular cartilage is removed and larger portions of the articular surfaces are decorticated (necessitating further, per se known tools, which are preferably used before fixation of the guide bush 21 and possibly the facet finder 20).

The tissue between the two bores is not removed (use of the cutter guide 24 and the cutter 25 may be eliminated).

The stabilization portion and/or the anchorage portions are made of a resorbable material to be gradually replaced by bone growth during resorption.

Figure 12:
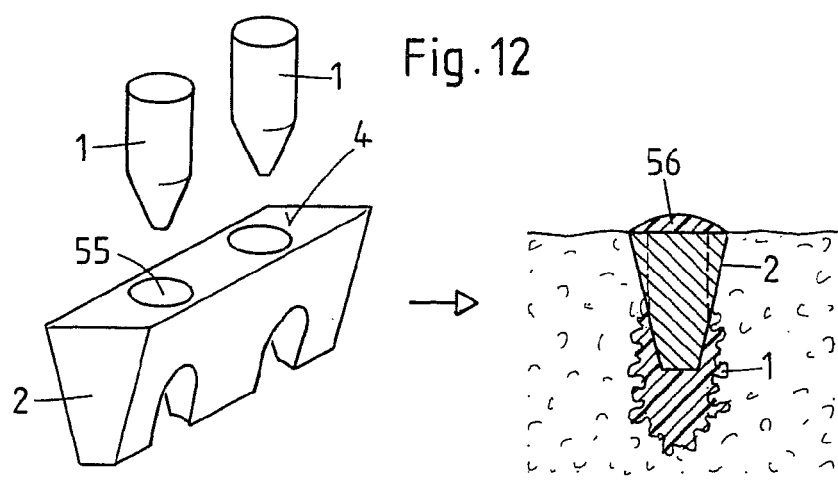
FIG. 12 shows a further exemplary embodiment of the fusion device according to the invention, the device comprising three separate parts to be introduced in the joint in succession and to be assembled within the joint (three-part or multi-part device)

The fusion device is a three-part (or multi-part) device comprising two (or more than two) anchorage portions and one stabilization portion constituting three (or more than three) separate device parts, wherein the stabilization portion is first positioned between the articular surfaces and the anchorage portions are then pushed through or past the stabilization portion to be anchored in the bone tissue and possibly in the stabilization portion (see also FIGS. 12 to 14; necessitating a second vibration tool if the stabilization portion comprises a liquefiable material and is to be anchored in the tissue of the articular surfaces, or necessitating a suitable punch, if the stabilization portion is made of a non-liquefiable material and is impacted into the gap between the articular surfaces).

The fusion device is a three-part device comprising two anchorage portions and one stabilization portion constituting three separate device parts, wherein the anchorage portions are first implanted (preferably simultaneously) and the stabilization portion is then fixed to the two proximal faces of the implanted anchorage portion (necessitating a second vibration tool if the stabilization portion comprises a liquefiable material and is fixed to the anchorage portions by ultrasonic welding, or necessitating a suitable punch, if the stabilization portion is made of a non-liquefiable material and is impacted into the proximal faces of the implanted anchorage portions).

The fusion device comprises two separate anchorage portions and no stabilization portion, wherein the two anchorage portions are preferably implanted simultaneously (use of cutter guide 24 and cutter 25 can be eliminated).

The fusion device comprises one anchorage portion and no stabilization portion (drill guide 22 and vibration tool 27 may possibly be adapted, use of cutter guide 24 and cutter 25 can be eliminated).

The anchorage portion(s) comprise the liquefiable material on one side only and/or the cartilage is removed from only one articular surface, such that the anchorage portion(s) is anchored only in one articular surface (possibly necessitating adaptation of the drill guide 22 and drill 23 as well as cutter guide 24 and cutter 25).

The one- or three-part fusion device is not anchored in the bone tissue but is simply pushed between the two articular surfaces, wherein the anchorage portions of the fusion device may comprise barbs, resilient protrusions or other per se known retaining means; in a three-part fusion device, the separate anchoring portions may be equipped with a thread and be pushed between the articular surfaces under rotation (the vibration tool 27 may be adapted to be a simple positioning tool or may not be vibrated but e.g. rotated for the implantation step).

The one- or three-part fusion device is anchored in the bone tissue using electromagnetic radiation (preferably in the visible or infrared frequency range) instead of vibration energy for liquefaction of the liquefiable material. For this purpose, instead of the vibration tool 27, a non-vibrating positioning tool is used, the positioning tool having the same form as the vibration tool and further comprising light guides with proximal ends being connected to a radiation source (e.g. laser) and distal ends arranged at the distal tool face in a manner suitable for coupling the laser light into the anchorage portions of the fusion device. Furthermore, the anchorage portions are designed to comprise in a central region a material which is transparent for the laser light and capable of scattering it, and near the surfaces where liquefaction is to occur a material capable of absorbing the laser light for creating the thermal energy needed for the liquefaction and anchoring. The anchorage portions consist e.g. of one thermoplastic material which in a pure state is transparent for the laser light and which in the central region contains a scattering agent and in a peripheral region an absorbing agent, the agents being e.g. particulate or molecular. In FIG. 7, the left hand side of the tool is shown comprising a light guide 45 (dash-dot lines) and the left hand anchorage portion comprising a central region 46 with a scattering agent (indicated by short lines of varying orientation) and a surface region 47 with an absorbing agent (indicated by small circles). The two agents need to be adapted in a per se known manner to the electromagnetic radiation to be coupled into the anchorage portion. The radiation source is activated shortly before, during or after the device is positioned between the articular surfaces. During liquefaction, a pressing force is applied to the pushing tool for making the liquefied material penetrate into the bone tissue.

Figure 19:
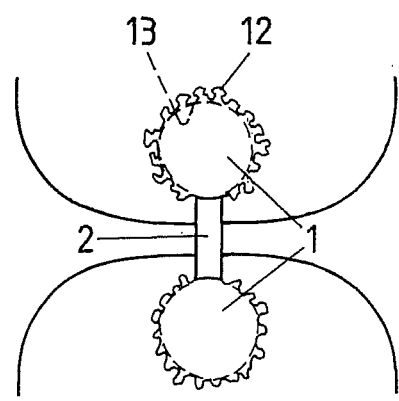
FIGS. 19 and 20 illustrate implantation of a fusion device comprising two anchorage portions and a stabilization portion, wherein the fusion device is not implanted between the articular surfaces but across the gap between the articular surfaces.
Figure 20:
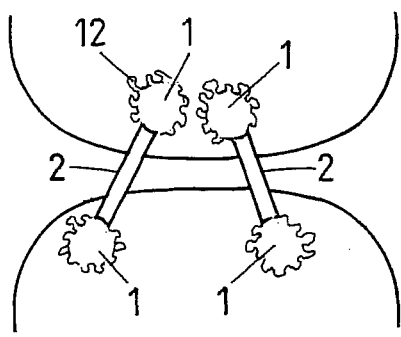

The one- or three-part fusion device comprising two anchorage portions and one stabilization portion is implanted with its width oriented perpendicular or at an oblique angle to the articular surfaces, i.e. not in the gap between the articular surfaces but across it (see also FIGS. 19 and 20; necessitates adaptation of the gap finder 20 by orienting the protrusions non-parallel to the largest cross section diameter but e.g. perpendicular to it).

FIG. 8 is a three-dimensional illustration of a fusion device based on the same principle as the device illustrated in FIGS. 1A to 1C. The fusion device comprises two anchorage portions 1 and one stabilization portion 2, arranged between the anchorage portions 1. The whole device is preferably made of a resorbable thermoplastic polymer (e.g. of polylactide, preferably LR706 by Böhringer). The anchorage portions 1 are slightly tapering and comprise a pointed distal end, the surface of the slightly tapering region being equipped with energy directors e.g. in the form of short axial ridges arranged in a plurality of adjacent rings, wherein the ridges of one ring are staggered in relation to the ridges of the adjoining ring or rings. Similar arrangements of energy directors are described in the publication US 2008/0109007 whose content is enclosed herein by reference. The fusion device is preferably implanted using vibrational energy, wherein the bores provided in the articular surfaces are preferably stepped and wherein the device and the bores and the tissue removal therebetween are preferably dimensioned such that liquefaction and anchorage between device and bone tissue occurs not only on the surface of the anchorage portions 1, but also on the surface of the stabilization portion 2. This means that the device is slightly oversized in comparison with the prepared joint gap, but because of the liquefaction no press-fit is achieved. On the other hand it is of course possible also to implant the same device without liquefaction, i.e. by simply impacting the device into the prepared joint gap where the device is retained by a press fit at least in the region of the anchorage portions.

The openings 5 extending axially from the proximal device face into the anchorage portion serve for holding the device on the distal end of a vibration or positioning tool, as discussed in connection with FIGS. 1A to 1C. In the case of a fully thermoplastic and therewith x-ray transparent fusion device, it is advantageous to design these openings deeper and to position marker elements therein. These marker elements comprise a material which is visible e.g. for an x-ray control of the device position after implantation. They consist e.g. of titanium, tantalum or another suitable metal or they comprise a bioresorbable material, such as e.g. a composite material of barium sulfate in PLA, which is eventually resorbed together with the rest of the fusion device.

If a fusion device, which is fully made of a suitable thermoplastic material, in particular of such a material having a relatively low glass transition temperature, is implanted with the aid of vibrational energy or another suitable type of energy, it is possible to introduce enough of the energy for bringing portions of the material above the glass transition temperature (in addition to liquefying surface material) such that they are capable of being slightly deformed and therefore better adapted to the form of the implantation site. Such deformation may e.g. concern the anchorage portions which may e.g. become slightly bent such being better adapted to articular surfaces without bores or to bores having non-straight axes due to slight movement of the articular surfaces relative to each other during implantation or it may concern the stabilization portion.

Figure 9:
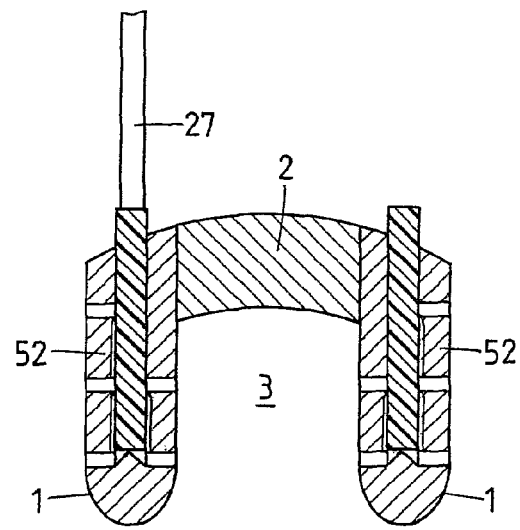
FIGS. 9 to 11 show further exemplary embodiments of the fusion device according to the invention, wherein in these embodiments the arrangement of the liquefiable material (and therewith the applicable anchoring technique) is different from the arrangement in the fusion device according to FIGS. 1A to 1C.

FIG. 9 shows a further exemplary embodiment of the fusion device according to the invention. The fusion device has approximately the same form as the fusion device shown in FIGS. 1A to 1C, but the anchorage portions 1 do not consist fully of the liquefiable material or comprise this material on their surfaces but they comprise a perforated sheath 52 each and the liquefiable material is provided inside these sheaths 52, e.g. in the form of a polymer pin.

The method for implanting the fusion device as shown in FIG. 9 is different from the method for implanting the fusion device as shown in FIGS. 1A to 1C in that the fusion device needs to be positioned between the prepared articular surfaces and only then the liquefiable material is liquefied by being pressed into the sheath 52 and simultaneously being impinged with mechanical vibration. On liquefaction, the material is pressed through the perforated walls of the sheaths 52 to penetrate into the bone tissue in the liquid state. For such liquefaction and pressing out, a vibration tool 27 is applied to the liquefiable material only, which vibration tool 27 may comprise a forked distal end equipped for holding and guiding the fusion device on being introduced into the joint and for transmitting vibrational energy to the liquefiable material of both anchorage portions 1 simultaneously. It is also possible to employ separate tools for positioning the fusion device and for vibrating the liquefiable material, wherein the vibration tool may have only one distal end (as illustrated) and the two anchorage portions are anchored in the bone tissue one after the other.

It is also possible to use mechanical vibration not only for liquefying the liquefiable material contained in the sheaths 52 but also for facilitating the positioning of the fusion device according to FIG. 9 between the prepared articular surfaces, which is achieved by using an additional vibration tool (not shown) suitable for transmitting the vibration to the sheaths of the anchorage portions and/or to the stabilization portion (vibration tool 27 e.g. as shown in FIG. 7).

It is also possible to first position the fusion device between the articular surfaces without the liquefiable material being present in the sheaths 52 using a corresponding positioning or vibration tool and only then introducing the liquefiable material constituted by two polymer pins adapted to the inner cross section and length of the sheaths 52 and applying the vibrational energy thereto.

The embodiment as shown in FIG. 9 also allows using a bone cement instead of the liquefiable material, or a polymer of a high viscosity, wherein the cement or polymer is made to harden when pressed out of the sheath and into the bone tissue of the articular surfaces.

Instead of vibrating the liquefiable material positioned in the sheaths 52, it is possible also to couple a pin comprising the liquefiable material to a rotation drive, to introduce a distal portion of the pin into the sheath 52 and to liquefy the material by rotating the pin within the sheath 52 and at the same time pressing it into the sheath and holding the sheath for preventing it from rotating with the rotating pin, such creating friction at least at the distal pin end and therewith thermal energy which liquefies the pin material.

Furthermore, as already mentioned in connection with the fusion device according to FIGS. 1A to 1C and 7, it is possible also to couple, instead of vibrational or rotational energy, electromagnetic radiation (preferably of the visible or infrared frequency range) into the liquefiable material which is e.g. equipped for scattering the radiation and transmitting it into the sheath (e.g. made of metal) where it is absorbed to create thermal energy which is able to liquefy the thermoplastic material at least partly. Absorption may also take place within the pin which for this purpose contains an absorbing agent. It is possible also to design the sheath such that at least an inner surface thereof can be heated electrically.

Figure 10:
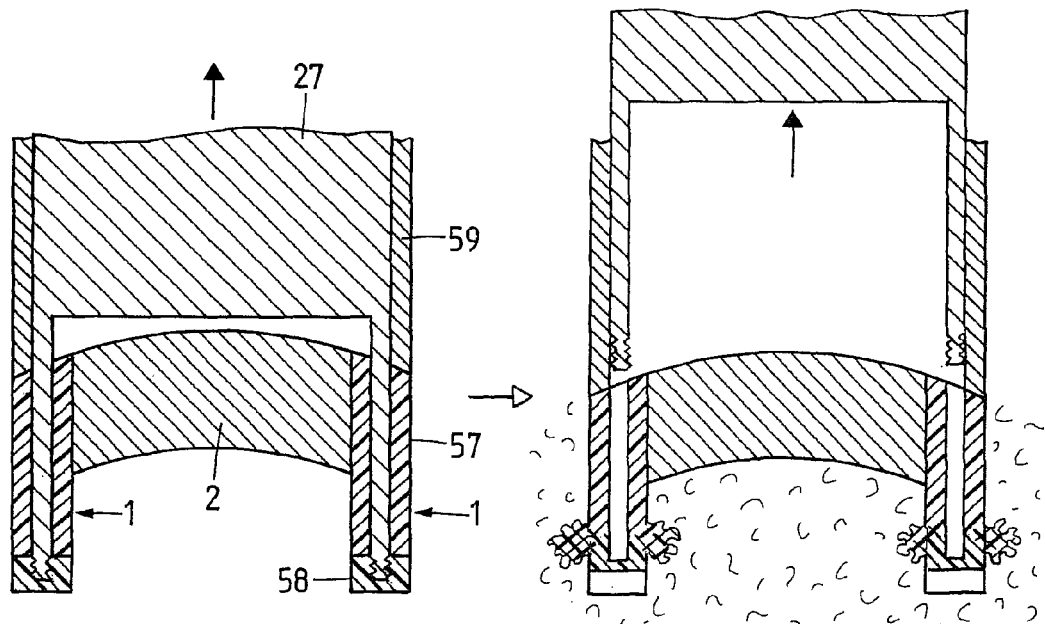

FIG. 10 shows a further exemplary embodiment of the fusion device according to the invention and the distal end of a vibration tool 27 suitable for implantation of the fusion device. The anchorage portions of the fusion device are anchored in the bone tissue of the articular surfaces using the anchoring technique as described in the publication WO 2009/055952. The anchorage portions 1 have the form of polymer tubes 57 and distal ends of the vibration tool 27 protrude through the tubes 57 and, adjacent to the distal ends of the tubes, carry distal foot pieces 58 which consist of the same polymer material as the tubes 57 or of a different polymer material being weldable to the polymer material of the tubes. This is shown on the left hand side of FIG. 10.

The foot pieces 58 are fixed to the vibration tool 27 via a connection (e.g. threads) which is able to transmit the vibrational energy from the tool 27 to the foot piece 58 and which is capable of being destroyed when the foot piece 58 is sufficiently warmed by the vibrational energy.

For the implantation, the fusion device as shown in FIG. 10 is held and guided between the articular surfaces with the aid of the vibration tool 27 and is held in place by a counter element 59. The vibration tool 27 is then vibrated and simultaneously pulled in a direction away from the fusion device. Through the vibrational energy, the liquefiable material of the distal end of the tubes 57 and/or of the proximal face of the foot pieces 58 is liquefied and penetrates into the bone tissue. Therewith the tubes 57 get shorter and are eventually welded to the foot pieces 58. As soon as a sufficient amount of the liquefiable material is liquefied and the foot pieces 58 are warm enough, the pulling force on the vibration tool 27 is increased for separating the distal tool ends from the foot pieces 58, which remain anchored in the bone tissue to constitute distal ends of the anchorage portions 1 as shown on the right hand side of FIG. 10.

A similar implantation result can be achieved by using, instead of vibrational energy, electromagnetic radiation which is coupled e.g. through the counter element 59 into the polymer tube 57 or through a pushing tool of the same form as the illustrated vibration tool 27 into the foot piece 58 to be absorbed in a distal part of the polymer tube 57 or in the foot pieces 58 of the tool, in the same manner as described for the fusion device as illustrated in FIGS. 1A to 1C and 7.

Figure 11:
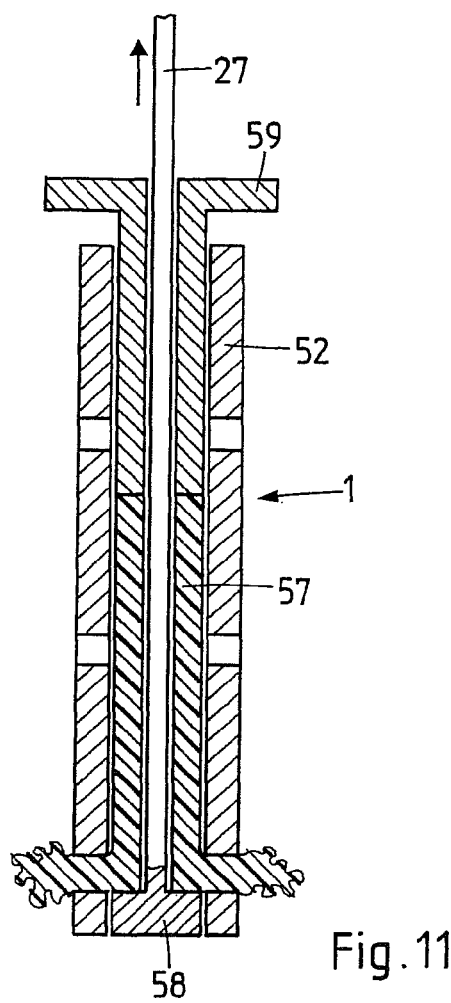

FIG. 11 shows an anchorage portion 1 of a further exemplary embodiment of the fusion device according to the invention as well as a distal end portion of a vibration tool 27 suitable for implantation of the fusion device. The fusion device may have a similar form as the fusion device according to FIGS. 1A to 1C. The anchorage portion 1 of the fusion device is designed for being anchored in the bone tissue of the articular surfaces using the anchoring technique as described in the provisional U.S. application No. 61/049, 587, the content of which is enclosed herein by reference. This anchoring technique is a combination of the anchoring techniques as shortly described in connection with FIGS. 9 and 10. For this reason, the anchorage portion 1 comprises a perforated sheath 52 and the liquefiable material is provided inside the sheath 52 in the form of a polymer tube 57 through which the distal end of the vibration tool 27 reaches, carrying a distal foot piece 58 beyond the polymer tube 57. The polymer tube 57 is held in place inside the sheath 52 with a counter element 59. For anchoring it in bone tissue, the anchorage portion 1 as shown in FIG. 11 is positioned between the suitably prepared articular surfaces of the joint to be fused, the polymer tube being held in place with a counter element 59. Then, the vibration tool 27 is pulled in a direction away from the bone tissue and is vibrated, such that the polymer material is liquefied between the distal face of the polymer tube 57 and the proximal face of the foot piece 58 and is pressed through the sheath perforations to penetrate into the bone tissue outside the sheath 52. Therein it is possible to equip the sheath with perforations at a plurality of distinct depths and to liquefy polymer material in these distinct depth in distinct liquefaction steps between which the foot piece is moved from one such depth to a next higher one, the vibration being switched off. After a last liquefaction step the counter element 58 and the vibration tool 27 are removed from the sheath 52, wherein a rest of the polymer tube 57 and the foot piece 58 remain in the sheath 52 (similar to the anchoring process as described in connection with FIG. 10) or are removed from the sheath. In the latter case the foot piece 58 may, as illustrated, be made of a non-liquefiable material.

In the same manner as described further above for the fusion devices as illustrated in FIGS. 1A to 1C, and 7 to 10, implantation of the fusion device comprising anchorage portions as illustrated in FIG. 11 is possible also with the aid of radiation energy (preferably laser light of the visible or infrared frequency range) or rotational energy instead of the above described vibrational energy. For the latter case, a pushing tool of the same form as the above described vibration tool 27 is used and the pushing tool is connected to a rotation drive, while the counter element 59 is equipped for not only holding the polymer tube 57 against the foot piece 58 but also for preventing the polymer tube from rotating together with the tool. Friction heat created between the distal face of the non-rotating polymer tube 57 and the proximal face of the rotating foot piece 58 liquefies the distal end of the polymer tube and makes the liquefied material pass through the perforations of the sheath 52. Furthermore, liquefaction can be achieved by coupling electromagnetic radiation e.g. into the counter element 59 and from there into the polymer tube 57 to be absorbed in the polymer tube 57 or in the foot piece 58. A further way for creating the thermal energy needed for the liquefaction consists in electrically heating the proximal face of the foot piece 58.

FIG. 12 shows a further embodiment of the fusion device according to the invention which fusion device, when implanted, resembles the fusion device according to FIGS. 1A to 1C or 7, but before implantation comprises the anchorage portions 1 and the stabilization portion 2 as separate parts (three-part device or possibly multi-part device). The stabilization portion 2 is designed for being introduced into the gap between the articular surfaces and for being then fixed by introducing the anchorage portions 1 (preferably simple polymer pins) through bores 55 in the stabilizing portion 2 and anchoring them then in the bone tissue. The stabilization portion 2 is preferably substantially wedge shaped and comprises two (or more than two) through bores 55 extending from the proximal face 4 to a distal face and preferably having a diameter which is smaller than the thickness of the stabilization portion 2 at the proximal face 4 and larger than the thickness of the stabilization portion 2 at the distal face such that the distal bore mouths extend from the distal face onto the lateral surfaces of the stabilization portion 2 towards the proximal face.

FIG. 12 shows on the left hand side the anchorage portions 1 before being introduced in the bores 55 of the stabilization portion 2, i.e. it shows the fusion device before implantation, and on the right hand side a section through the fusion device after implantation. For the anchorage portions 1 being able to fix the stabilization portion 2 firmly in the gap between the articular surfaces, it is advantageous to provide in the bores 55 of the stabilization portion 2 a further liquefiable material which is welded to the liquefiable material of the anchorage portions on implantation, or a surface structure, into which the liquefiable material of the anchorage portions is pressed on implantation. A similar effect can be achieved by equipping the anchorage portions 1 with heads, or, as illustrated, to form such heads 56 by applying further vibrational energy for plasticizing and correspondingly deforming the material of the proximal end of the anchorage portions 1.

For providing the grooves in the bone tissue of the articular surfaces for accommodating the distal ends of the anchorage portions, it is possible to use a drill guide as shown in FIG. 4C or to use the positioned stabilization portion 2 of the device as drill guide.

As already described for the fusion device as illustrated in FIGS. 1A to 1C and 7, it is possible for the fusion device according to FIG. 12 to use for the implantation or the liquefaction of the liquefiable material respectively, instead of vibrational energy, electromagnetic radiation and to provide means for absorbing such radiation in or adjacent to the location in which such liquefaction is desired. For such purpose, the stabilization portions 1 comprise an absorbing agent or the radiation is absorbed by the stabilizing portion 2.

Instead of the anchorage portions as illustrated in FIG. 12 to be anchored in bores between the articular surfaces and possibly welded in the stabilization portion with the aid of a liquefiable material and e.g. vibrational energy, it is possible also to use anchorage portions as illustrated in FIGS. 9 to 11 or per se known interference screws.

FIGS. 13A to 13D show further embodiments of the three-part or multi-part fusion device according to the invention, the embodiments being based on the same principle as the fusion device according to FIG. 12. A first embodiment is illustrated in FIGS. 13A (viewed from the side of the proximal face, after implantation) and 13B (in section, section plane designated with B-B in FIG. 13A, in partly implanted state), and a second embodiment is illustrated in FIGS. 13C (viewed from the side of the proximal face, after implantation) and 13D (in section, section plane designated with D-D in FIG. 13C, before and after implantation). In contrast to the fusion device illustrated in FIG. 12, the anchorage portions 1 of the devices according to FIGS. 13A to 13D do not extend through openings in the stabilization portion 2 but are positioned on both sides of the stabilization portion, wherein a bore (or opening with another than circular cross section) adapted to receive one of the anchorage portions is preferably situated partly in the stabilization portion (groove 60) and partly in the bone tissue (opening 11, being groove in a proximal region).

As for the fusion device according to FIG. 12, the fusion devices according to FIGS. 13A to 13D are implanted by firstly pushing the stabilization device into the joint gap and by then positioning the anchorage portions and anchoring them in the bone tissue. Therein the opening/grooves 11 to be provided in the bone tissue of the articular surfaces may be made before positioning the stabilization portion 2 in the joint gap using a drill guide e.g. as illustrated in FIG. 4C or they may be made after positioning the stabilization portion 2 in the joint gap, using the stabilization portion as a drill guide.

The anchorage portions 1 of the fusion devices according to FIGS. 13A to 13D are again anchored in the bone tissue with the aid of a liquefiable material, wherein the liquefiable material is arranged on the anchorage portions in any of the ways as discussed further above. Therein it is advantageous to simultaneously, with the anchoring in the bone tissue, connect the anchorage portions with the stabilization portion, e.g. by providing a suitably structured surface on the stabilization portion where the anchorage portions are to be attached and by providing the liquefiable material on both sides of the anchorage portions, on one side for establishing a positive fit connection with the bone tissue and on the other side for establishing a positive fit connection with the surface structure of the stabilization portion 2. Further examples of methods for in situ attaching device parts to each other and simultaneously anchoring them in bone tissue are described in the publication WO 2008/034276 which is incorporated herein in its entirety by reference. Further such methods are discussed in connection with FIGS. 14A to 14C.

The fusion device according to FIGS. 13A and 13B comprises one stabilization portion 2 and four anchorage portions 1, wherein the stabilization portion 2 has e.g. the form of a wedge and comprises two grooves 60 on either side for receiving the anchorage portions 1. The fusion device according to FIGS. 13C and 13B differs from the fusion device according to FIGS. 13A and 13B by two anchorage portions being connected with a bridge element 61 to form a twin anchorage portion 1'.

The stabilization portions of the devices according to any of FIGS. 12 to 13D are positioned in the joint gap by being pushed in with the aid of a positioning tool. It is possible also to use a screw arrangement cooperating with a thread which is provided in a through opening of the stabilization portion 2. Therein, the screw arrangement is to be supported on the bone tissue such that there is no axial displacement of the screw relative to the bone and, on rotating the screw, the stabilization portion is moved along the screw into the joint gap (cork screw principle).

Figure 14A:
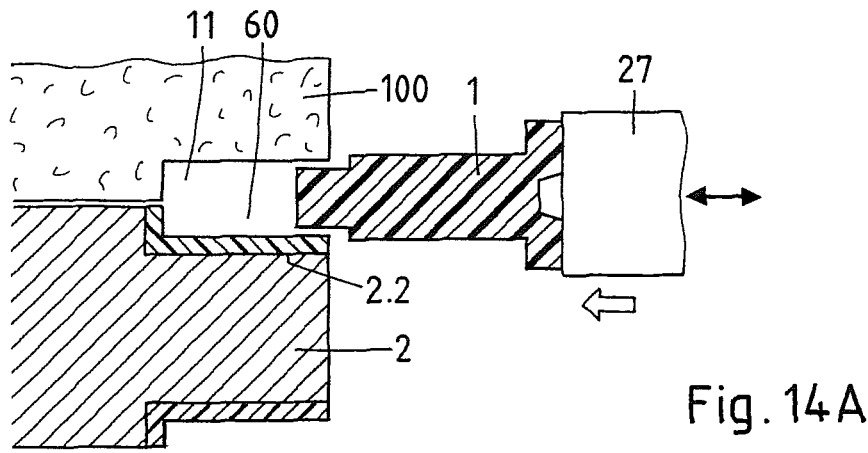
FIGS. 14A to 14C illustrate methods for connecting in situ the anchorage portions with the stabilization portions of the fusion devices according to FIG. 12 or FIGS. 13A to 12D.
Figure 14B:
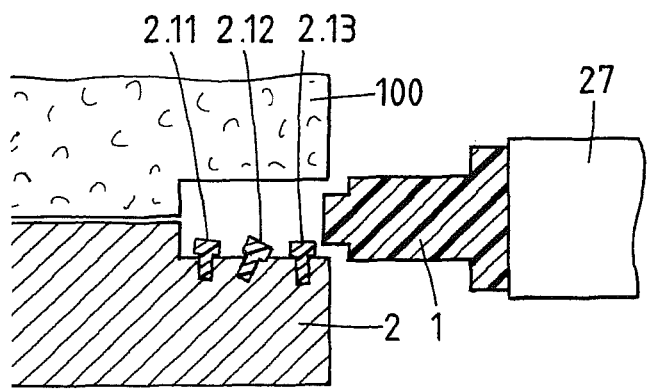
Figure 14C:
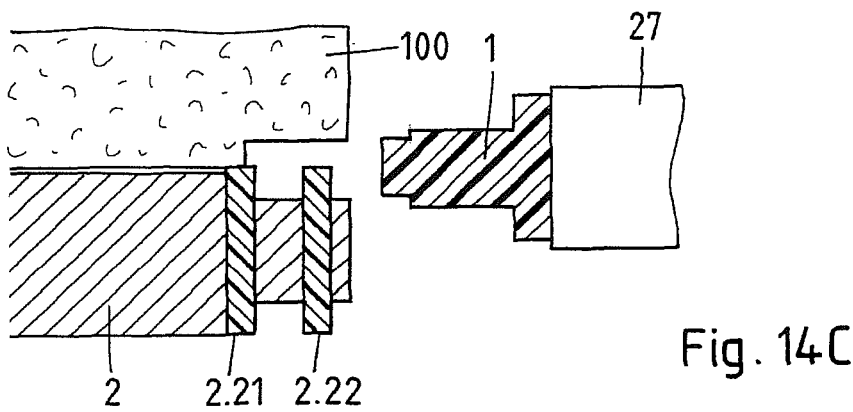

FIGS. 14A to 14C illustrate a further method for anchoring the anchorage portions 1 of the devices as illustrated in FIGS. 12 to 13D in the bone tissue and at the same time welding them to the stabilization portion 2. For this purpose, the stabilization portion comprises a liquefiable material at least in surface regions to be attached to anchorage portions 1, wherein this liquefiable material is to be weldable to the liquefiable material of the anchorage portions. All FIGS. 14A to 14C show the bone in section parallel to the implantation direction, part of the stabilization portion 2, the bone tissue 100 on one side of the stabilization portion 2 and one anchorage element 1 ready for being positioned between the bone tissue 100 and the stabilization portion 2 and simultaneously being anchored in the bone tissue of the articular surface and welded to the stabilization portion 2. Therein for positioning the anchorage element 1, a groove 11 is provided in the bone tissue 100 and an opposite groove 60 in the stabilization portion 2.

According to FIG. 14A, at least the region of the groove 60 of the stabilization portion 2 comprises a coating 2.2 to which the liquefiable material of the anchorage portion is weldable under the implantation condition, e.g. when the anchorage portion is pushed into the opposite grooves and simultaneously vibrated (e.g. ultrasonic vibration). According to FIG. 14B, a plurality of thermoplastic pins 2.11, 2.12, 2.13 is arranged in the groove 60 of the stabilization portion 2 instead of the coating 2.2. It may be advantageous to arrange the thermoplastic pins 2.11, 2.12, 2.13 at different angles. According to FIG. 14C, the stabilization portion 2 carries one or a plurality of thermoplastic inserts 2.21, 2.22, comprising portions which protrude into groove 60 and being suitable for being welded to the anchorage portion 1.

FIGS. 15 to 18 show further exemplary embodiments of the fusion device according to the invention, the devices comprising numbers of anchoring portions and/or stabilization portions which are different form such numbers of the embodiment according to FIGS. 1A to 1C. Virtually all above comments regarding the fusion device, in particular the various designs of the anchorage portions as shown in FIGS. 7 to 11, the corresponding anchoring techniques, and the design of multi-part devices as illustrated in FIGS. 12 to 13D are adaptable to these further embodiments of the fusion device in a straight forward manner.

Figure 15:
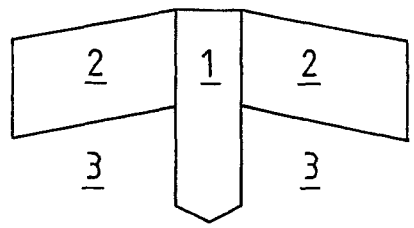
FIGS. 15 to 18 show further exemplary embodiments of the fusion device according to the invention, which fusion devices comprise numbers of anchorage portions and stabilization portions which are different from these numbers of the fusion device according to FIGS. 1A to 1C.

The fusion device according to FIG. 15 comprises only one anchorage portion 1 and two stabilization portions 2, which are arranged on lateral sides of the anchorage portion 1, opposite each other and in a proximal region of the anchorage portion 1. The fusion device delimits with concave contour areas two osteoconduction regions 3 being situated beside the distal region of the anchorage portion 1.

Figure 16:
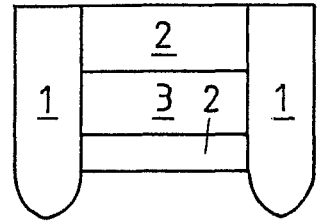

The fusion device according to FIG. 16 comprises two anchorage portions 1 and a two-part stabilization portion 2 therebetween, the osteoconduction region 3 being delimited between lateral sides of the anchorage portions 1 and distal and proximal faces of the two parts of the stabilization portion 2.

Figure 17:
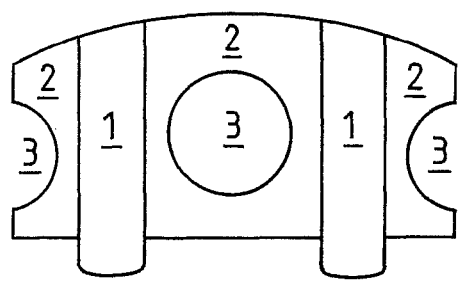

The fusion device according to FIG. 17 comprises two anchorage portions 1 and three stabilization portions 2, three osteoconduction regions 3 being defined by through openings in the stabilization portions 2.

Figure 18:
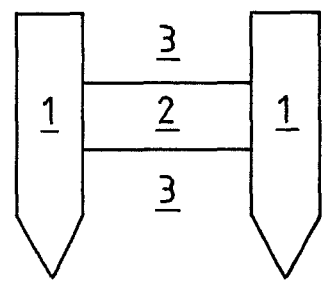

The fusion device according to FIG. 18 comprises two anchorage portions 1 and one stabilization portion 2 joined to the anchorage portion 1 in a central region between the distal and proximal ends thereof. Two osteoconduction regions 3 are delimited by proximal and distal regions of the anchorage portions 1 and proximal and distal faces of the stabilization portion 2.

FIGS. 19 and 20 illustrate the already above mentioned further embodiment of the method according to the invention, wherein a fusion device comprising two (or more than two) anchorage portions 1 and at least one stabilization portion 2 between anchorage portions is implanted not in the gap between the articular surfaces of the joint to be fused, but across this gap, i.e. the width of the fusion device being oriented at a right angle (FIG. 19) or at an oblique angle (FIG. 20) relative to the gap, the anchorage portions of the fusion device being anchored in openings 13 being provided in the bone tissue on either side of the gap between the articular surfaces and at a distance from the cartilage layer of the articular surfaces. Therein, for fusing one joint, one fusion device may be implanted (FIG. 19) or a plurality thereof (two fusion devices as shown in FIG. 20). The implantation process for fusing a joint as illustrated in FIGS. 19 and 20 is carried out in quite the same way as implantation as illustrated in FIGS. 2A to 2D. Therein tools similar to the tools shown in FIGS. 4A to 4H are applicable, the gap finder being adapted such that the arrangement of the gap finding protrusions is oriented at a right or oblique angle to the longest cross section extension of the tool.

Implantation as illustrated in FIGS. 19 and 20 is particularly advantageous for fusing synovial joints comprising articular surfaces with small radius curvatures and being exposed to relatively high torque loads, i.e. for synovial joints such as small pivot joints or saddle joints (e.g. human finger joints and toe joints), wherein a non-parallel arrangement of two fusion devices as illustrated in FIG. 20 further enhances the rigidity achieved by the arthrodesis.

Example

Fusion devices as shown in FIGS. 1A to 1C and dimensioned for fusion of a human facet joint were implanted between two pieces of "Saw Bone"™, each one comprising two grooves for accommodating the anchorage portions of the fusion device. The fusion devices consisted fully of PLDLA and were pushed between the saw bone pieces with the aid of an ultrasonic handpiece of Branson (Branson LPe 20 kHz, 150 W with converter TW1 and Branson LPe 30 kHz, 500 W with converter Palm). Good anchorage results were achieved with amplitudes of 20 to 40 micrometers (measured on the distal side of the implant), a power of 10 to 60 W and pushing forces in the range of 30 to 50N. Therein implantation with 20 kHz seemed more advantageous as the fusion device remained fully rigid throughout the implantation process, in particular no softening in the region of the proximal device face was observed.

What is claimed is:

1. A fusion device for fusing a joint of a human or animal patient, wherein the joint is a synovial joint comprising two articular surfaces between two bones and a gap therebetween, the fusion device comprising:
   at least one anchorage portion and at least one stabilization portion,
   wherein the fusion device has an overall depth parallel to an implantation direction, the overall depth extending from a proximal face to a distal end of the fusion device, an overall width and a thickness profile perpendicular to the implantation direction,
   wherein the at least one anchorage portion and the at least one stabilization portion are arranged or arrangeable alternating over the width, the at least one anchorage portion having a thickness that is greater than a thickness of the at least one stabilization portion,
   wherein the fusion device is capable of mechanically preventing articular movement of the joint to be fused immediately after implantation as well as preventing movements due to shearing forces in all directions, movements due to torque, and movements due to bending forces in planes other than articulating planes, while permitting micro movements of the two bones relative to each other that enhance osseointegration and osteoconduction,
   wherein the at least one anchorage portion comprises a material that is liquefiable from a solid state to a flowable state upon application of energy during or after introduction of the anchorage portion into bone tissue,
   wherein the liquefiable material is arranged on a surface of the anchorage portion or inside a perforated sheath constituting a part of the anchorage portion,
   wherein said surface of the anchorage portion or said perforated sheath is arranged on the fusion device for being in contact with bone tissue on implantation,
   wherein the liquefiable material is able to penetrate into pores, cavities or other structures of the bone tissue when in the flowable state and is able to form a positive fit connection with the bone tissue upon re-solidification,
   and wherein the fusion device comprises a proximal coupling structure for the fusion device to be held by a tool.

2. The fusion device according to claim 1, wherein the stabilization portion together with the anchorage portion forms a concave device contour and therewith delimits an osteoconduction region.

3. The fusion device according to claim 2, wherein a material furthering bone growth is arranged in the osteoconduction region, or device surfaces in the concave contour comprise means for holding such material.

4. The fusion device according to claim 3, wherein the material furthering bone growth is at least one of allograft or autograft bone material, a bone replacement material, a sponge, and a BMP carrier.

5. The fusion device according to claim 1, wherein the liquefiable material or a further device part adjacent to the liquefiable material is capable of absorbing electromagnetic radiation energy of the visible or infrared frequency range.

6. The fusion device according to claim 1, wherein the whole fusion device is made of the liquefiable material.

7. The fusion device according to claim 1, wherein the stabilization portion is equipped for furthering osseointegration by comprising surfaces which are equipped with a coating capable of enhancing osseointegration or a surface structure capable of enhancing osseointegration or both, a coating and a surface structure capable of enhancing osseointegration.

8. The fusion device according to claim 1, wherein a depth of the anchorage portion is larger than a depth of the stabilization portion.

9. The fusion device according to claim 8, comprising two pin-shaped anchorage portions and one stabilization portion, wherein the stabilization portion is arranged between the anchorage portions.

10. The fusion device according to claim 8, wherein the anchorage and stabilization portions constitute separate device parts and the stabilization portion is designed for being fixed to proximal ends of the anchorage portions and to extend therebetween.

11. The fusion device according to claim 8, wherein the stabilization portion comprises through openings or grooves for accommodating the anchorage portions.

12. The fusion device according to claim 1, wherein the proximal device face comprises at least one opening or protrusion or a convex curvature or both, at least one opening and a convex curvature.

13. The fusion device according to claim 1, wherein the liquefiable material is a material having thermoplastic properties, a modulus of elasticity of at least 0.5 GPa and a melting temperature of at the most 350° C.

14. The fusion device according to claim 1, comprising two of the anchorage portions and one stabilization portion, the stabilization portion being situated between the anchorage portions and connecting the anchorage portions, the stabilization portion and the anchorage portions together defining the proximal end face, the anchorage portions extending away from the proximal end face further than the stabilization portion, whereby a depth of the anchorage portions is larger than a depth of the stabilization portion.

15. The fusion device according to claim 14, wherein at least the anchorage portions comprise a material having thermoplastic properties and being liquefiable from a solid state to a flowable state, wherein outer surface portions of the anchorage portions comprise energy directors.

16. The fusion device according to claim 14, comprising axial openings or bores extending distally from the proximal end face.

17. The fusion device according to claim 14, wherein the proximal end face is convexly curved.

18. The fusion device according to claim 14 consisting of a resorbable thermoplastic material.

19. The fusion device according to claim 1 being one-piece.

20. The fusion device according to claim 1, comprising a coupling-in face equipped for being coupled to a vibration tool, wherein the liquefiable material is liquefiable by friction heat generated by mechanical vibration coupled into the fusion device via the coupling-in face while a pressing force is exerted on the coupling-in face.

21. The fusion device according to claim 20, wherein the coupling-in face comprises means for the fusion device to be held by the vibration tool.

22. The fusion device according to claim 21, wherein the means comprise axial openings or bores.

23. The fusion device according to claim 20, wherein the coupling-in face is the proximal face, and wherein the fusion device is equipped for transmitting the mechanical vibration from the coupling-in face to the surface of the anchorage portion.

24. The fusion device according to claim 20, wherein outer surfaces of the anchorage portions comprise energy directors to initiate a liquefaction process of the liquefiable material when the fusion device is subject to the mechanical vibration and a pressing force.

25. The fusion device according to claim 1, wherein the tool is a vibration tool.

26. The fusion device according to claim 1, wherein the proximal coupling structure comprises at least one axial opening or bore extending from the proximal face and cooperating with corresponding protrusions on a distal tool face.

27. The fusion device according to claim 26, wherein the proximal coupling structure comprises a pair of the axial openings or bores.

* * * * *